US012630488B2

(12) United States Patent
Echigo et al.

(10) Patent No.: US 12,630,488 B2
(45) Date of Patent: May 19, 2026

(54) HYDROCARBON PRODUCTION SYSTEM, AND PRODUCTION METHOD AND OPERATION METHOD THEREOF

(71) Applicant: Osaka Gas Co., Ltd., Osaka (JP)

(72) Inventors: Mitsuaki Echigo, Osaka (JP); Hisao Ohnishi, Osaka (JP); Yuji Tsuda, Osaka (JP)

(73) Assignee: Osaka Gas Co., Ltd., Osaka (JP)

( * ) Notice: Subject to any disclaimer, the term of this patent is extended or adjusted under 35 U.S.C. 154(b) by 803 days.

(21) Appl. No.: 17/914,128

(22) PCT Filed: Mar. 31, 2021

(86) PCT No.: PCT/JP2021/014082
§ 371 (c)(1),
(2) Date: Sep. 23, 2022

(87) PCT Pub. No.: WO2021/201191
PCT Pub. Date: Oct. 7, 2021

(65) Prior Publication Data
US 2023/0114967 A1 Apr. 13, 2023

(30) Foreign Application Priority Data

Mar. 31, 2020 (JP) ................................. 2020-065254

(51) Int. Cl.
*C07C 1/04* (2006.01)
*B01J 23/42* (2006.01)
(Continued)

(52) U.S. Cl.
CPC ............. *C07C 1/0445* (2013.01); *B01J 23/42* (2013.01); *B01J 23/462* (2013.01); *B01J 23/63* (2013.01);
(Continued)

(58) Field of Classification Search
CPC .......... B01J 23/42; B01J 23/462; B01J 23/63; B01J 23/745; B01J 23/755; C07C 1/0435;
(Continued)

(56) References Cited

U.S. PATENT DOCUMENTS

2006/0211777 A1 9/2006 Severinsky
2007/0149392 A1 6/2007 Ku et al.
(Continued)

FOREIGN PATENT DOCUMENTS

CA 3107254 A1 10/2019
CN 103183346 A 7/2013
(Continued)

OTHER PUBLICATIONS

Office Action issued in JP2022-512676 on Oct. 11, 2024.
Office Action issued in CN202180025218.0 on Aug. 24, 2023.
Office Action issued in JP2021160943 on Apr. 24, 2025.
Office Action issued in CA3,172,456 on Nov. 3, 2025.

*Primary Examiner* — Jafar F Parsa
(74) *Attorney, Agent, or Firm* — The Webb Law Firm

(57) ABSTRACT

As a hydrocarbon production system that synthesizes hydrocarbons using water and carbon dioxide as raw materials, a hydrocarbon production system capable of producing hydrocarbons by securing hydrogen and carbon monoxide required for hydrocarbon synthesis is provided. In a hydrocarbon production system that produces hydrocarbons from at least water and carbon dioxide, the hydrocarbon production system includes at least an electrolytic reaction unit, a reverse water-gas shift reaction unit, and a hydrocarbon synthesis reaction unit.

17 Claims, 7 Drawing Sheets

(51) Int. Cl.

| | |
|---|---|
| *B01J 23/46* | (2006.01) |
| *B01J 23/63* | (2006.01) |
| *B01J 23/648* | (2006.01) |
| *B01J 23/652* | (2006.01) |
| *B01J 23/745* | (2006.01) |
| *B01J 23/755* | (2006.01) |
| *B01J 23/83* | (2006.01) |
| *B01J 37/02* | (2006.01) |
| *C01B 32/40* | (2017.01) |
| *C07C 9/04* | (2006.01) |
| *C10G 2/00* | (2006.01) |
| *C25B 1/04* | (2021.01) |
| *C25B 1/23* | (2021.01) |
| *C25B 9/23* | (2021.01) |

(52) U.S. Cl.
CPC ......... *B01J 23/6482* (2013.01); *B01J 23/652* (2013.01); *B01J 23/745* (2013.01); *B01J 23/755* (2013.01); *B01J 23/83* (2013.01); *B01J 37/0201* (2013.01); *C01B 32/40* (2017.08); *C07C 1/0435* (2013.01); *C07C 9/04* (2013.01); *C10G 2/332* (2013.01); *C10G 2/333* (2013.01); *C25B 1/04* (2013.01); *C25B 1/23* (2021.01); *C25B 9/23* (2021.01)

(58) Field of Classification Search
CPC ............. C07C 9/04; C25B 1/04; C10G 2/232; C10G 2/333
See application file for complete search history.

(56) References Cited

U.S. PATENT DOCUMENTS

| | | | |
|---|---|---|---|
| 2010/0280135 A1 | 11/2010 | Doty | |
| 2013/0109767 A1 | 5/2013 | Bogild Hansen | |
| 2016/0053388 A1 | 2/2016 | Reytier et al. | |
| 2016/0296916 A1 | 10/2016 | Kim et al. | |
| 2018/0086984 A1* | 3/2018 | Chen ........................ | B01J 23/10 |
| 2019/0194816 A1 | 6/2019 | Brunot et al. | |
| 2020/0239381 A1 | 7/2020 | Ahougue et al. | |
| 2020/0406246 A1* | 12/2020 | Álvarez Galván ....... | C01B 3/16 |
| 2021/0119239 A1 | 4/2021 | Echigo et al. | |

FOREIGN PATENT DOCUMENTS

| | | | |
|---|---|---|---|
| JP | 2007196206 A | 8/2007 | |
| JP | 2008533287 A | 8/2008 | |
| JP | 2013119556 A | 6/2013 | |
| JP | 2014009166 A | 1/2014 | |
| JP | 2016522166 A | 7/2016 | |
| JP | 2018150254 A | 9/2018 | |
| JP | 2019035102 A | 3/2019 | |
| JP | 2019112717 A | 7/2019 | |
| JP | 2020121944 A | 8/2020 | |
| KR | 1020180097883 A | 9/2018 | |
| WO | 2006099573 A1 | 9/2006 | |
| WO | 2012003849 A1 | 1/2012 | |
| WO | 2019189912 A1 | 3/2019 | |
| WO | 2019077288 A1 | 4/2019 | |

\* cited by examiner

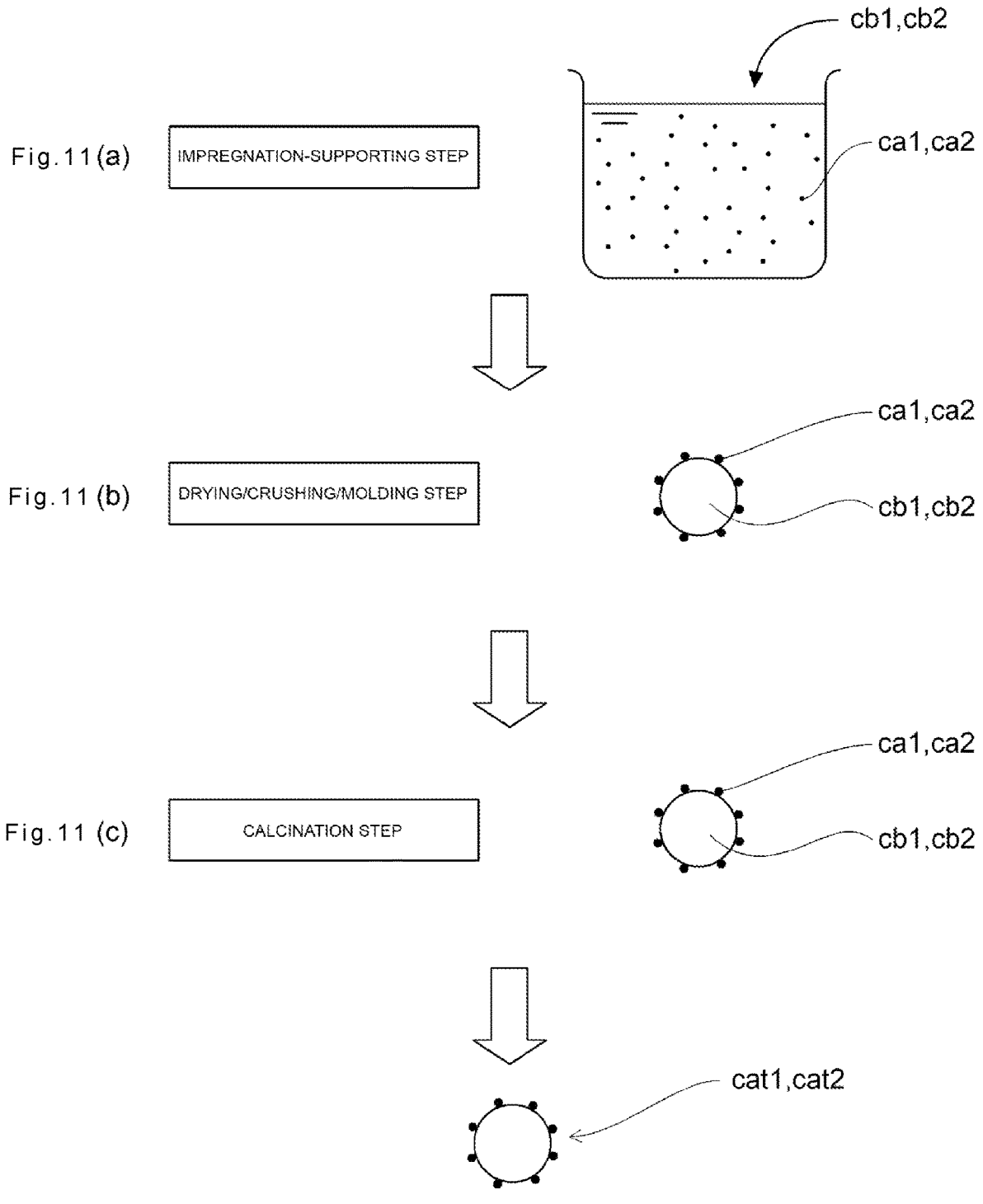
Fig.11(a) IMPREGNATION-SUPPORTING STEP
Fig.11(b) DRYING/CRUSHING/MOLDING STEP
Fig.11(c) CALCINATION STEP

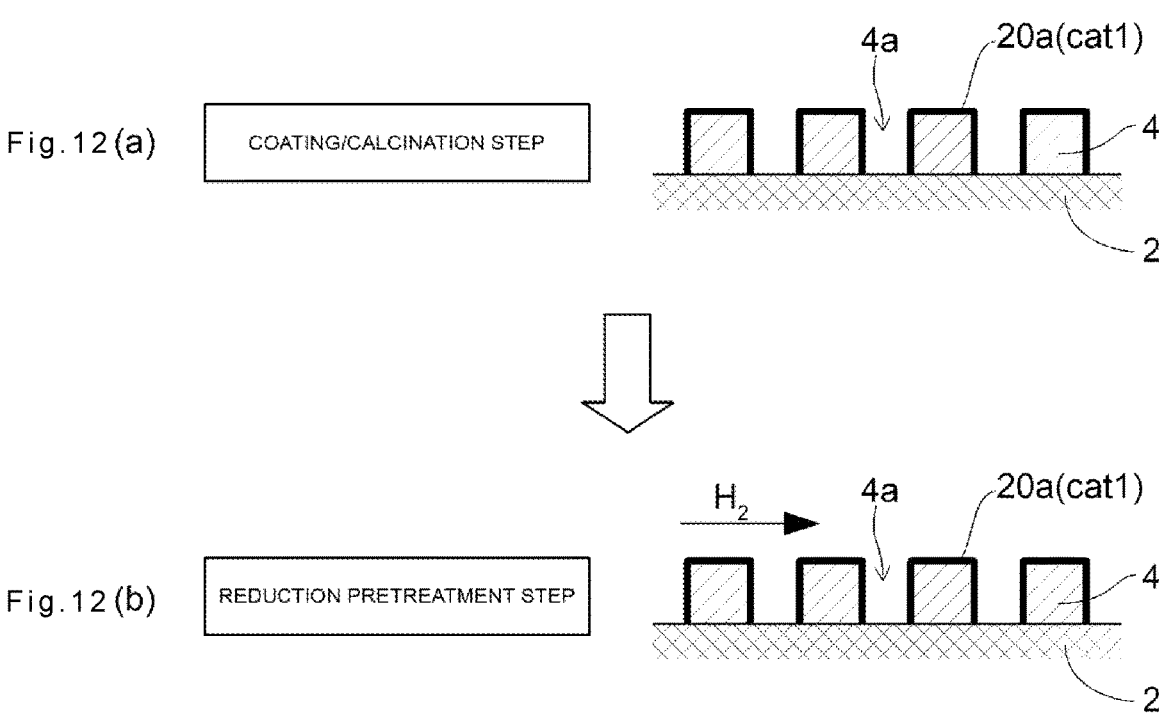
Fig.12(a) COATING/CALCINATION STEP
Fig.12(b) REDUCTION PRETREATMENT STEP
Fig.13
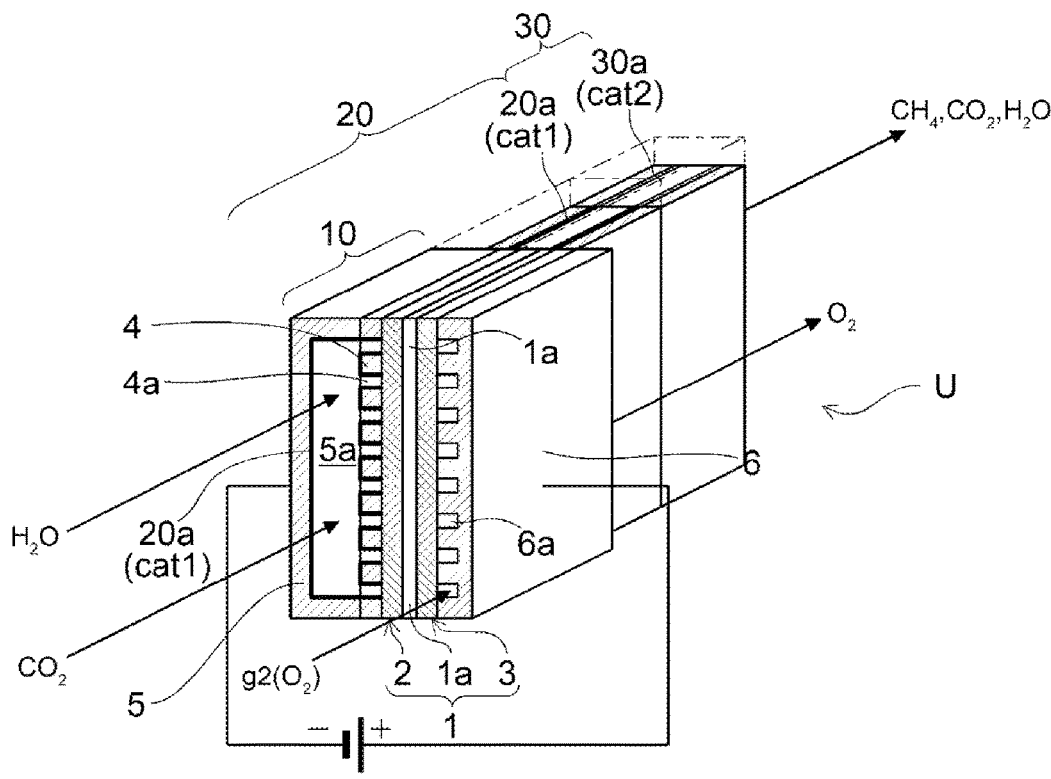

HYDROCARBON PRODUCTION SYSTEM, AND PRODUCTION METHOD AND OPERATION METHOD THEREOF

CROSS-REFERENCE TO RELATED APPLICATIONS

This application is the United States national phase of International Application No. PCT/JP2021/014082 filed Mar. 31, 2021, and claims priority to Japanese Patent Application No. 2020-065254 filed Mar. 31, 2020, the disclosures of which are hereby incorporated by reference in their entirety.

BACKGROUND OF THE INVENTION

Field of the Invention

The present invention relates to a hydrocarbon production system that produces hydrocarbons from at least water and carbon dioxide, and also relates to a production method and an operation method of the hydrocarbon production system.

Description of Related Art

This type of hydrocarbon production system is disclosed in JP-T-2016-522166 and JP-A-2019-112717.

The system disclosed in JP-T-2016-522166 includes a high temperature electrolyte (HTE) reactor (corresponding to electrolytic reaction unit of the present invention) including stacking of electrolytic single cells (corresponding to the electrolytic cell unit of the present invention) that generate either hydrogen or a synthetic raw material gas ("synthetic gas" representing a mixture of hydrogen and carbon monoxide) from steam and carbon dioxide, in which the synthetic gas obtained in this electrolytic single cell is converted into a desired combustible gas by a heterogeneous catalytic action.

Therefore, in the technique disclosed in JP-T-2016-522166, a hydrocarbon synthesis unit is provided on the downstream side of the electrolytic reaction unit, and hydrocarbons are synthesized (produced) using water and carbon dioxide as starting materials.

Meanwhile, a technique disclosed in JP-A-2019-112717 relates to a power-to-gas unit that generates a useful gas (specifically, methane) from electric power, specifically, a technique is disclosed in which a methanation reaction catalyst material is contained in a cathode of a stack of a solid oxide (SOEC) basic electrolytic cell.

Even in the technique disclosed in JP-A-2019-112717, the basic electrolytic cell serves as an electrolytic reaction unit, and the methanation reaction catalyst material provided on the cathode constitutes a hydrocarbon synthesis unit.

In the related arts, in the electrolytic reaction unit, so-called "co-electrolysis" is carried out in which both water and carbon dioxide are electrolyzed together. A heterogeneous catalyst is used for synthesis (so-called methanation) of hydrocarbons.

However, it has been found that there are the following problems regarding co-electrolysis in the electrolytic (electrolysis) reaction unit and hydrocarbon synthesis in the hydrocarbon synthesis unit.

1. Problems of Co-Electrolysis

Since an electrolytic (electrolysis) voltage of water is around 1.23 V, while an electrolytic voltage of carbon dioxide is around 1.33 V, the electrolytic (electrolysis) reaction of carbon dioxide is less likely to occur than the electrolytic reaction of water. As a result, even when the co-electrolysis reaction is attempted, the electrolytic reaction of carbon dioxide is unlikely to occur, and the concentration of carbon monoxide required for hydrocarbon synthesis cannot be sufficiently secured.

2. Problems in Hydrocarbon Synthesis

It is said that a heterogeneous catalyst is used as the catalyst for the hydrocarbon synthesis, but it is difficult to select this kind of catalyst, and a technique capable of stably synthesizing hydrocarbon has not yet been established.

SUMMARY OF THE INVENTION

In view of this situation, a main subject of the present invention is to obtain a hydrocarbon production system capable of producing hydrocarbon by securing hydrogen and carbon monoxide required for hydrocarbon synthesis in a hydrocarbon production system that synthesizes hydrocarbons using water and carbon dioxide as raw materials.

According to a first characteristic configuration of the present invention, there is provided a hydrocarbon production system that produces hydrocarbons from at least water and carbon dioxide, the hydrocarbon production system including at least an electrolytic reaction unit, a reverse water-gas shift reaction unit, and a hydrocarbon synthesis reaction unit.

In this hydrocarbon production system, the electrolytic reaction unit, the reverse water-gas shift reaction unit, and the hydrocarbon synthesis reaction unit are provided. In this configuration, a spatial positional relationship between units is not questioned, but at least with respect to a gas flowing between the units, a gas decomposed in the electrolytic reaction unit flows to the reverse water-gas shift reaction unit, and hydrogen and carbon monoxide obtained through a reaction in the unit may flow to the hydrocarbon synthesis reaction unit to synthesize hydrocarbons.

That is, in the electrolytic reaction unit, the gas supplied to this unit is decomposed to obtain at least hydrogen. In the reverse water-gas shift reaction unit, carbon monoxide is generated from carbon dioxide, and carbon monoxide required for hydrocarbon synthesis in the hydrocarbon synthesis reaction unit is obtained by this reaction. As a result, in addition to the hydrogen obtained in the electrolytic reaction unit, carbon monoxide generated in the reverse water-gas shift reaction unit can be used to efficiently obtain hydrocarbons in the hydrocarbon synthesis reaction unit.

Therefore, even when carbon monoxide is not satisfactorily generated in the electrolytic reaction unit, sufficient carbon monoxide can be secured by providing the reverse water-gas shift reaction unit.

Further, although the electrolytic reaction unit is a reaction at a high temperature, system efficiency can be improved by combining the reverse water-gas shift reaction unit, which is an endothermic reaction, with the electrolytic reaction unit.

In a second characteristic configuration of the present invention, an electrolytic reaction of water is carried out in the electrolytic reaction unit.

According to this characteristic configuration, hydrogen required in the hydrocarbon synthesis reaction unit can be obtained by electrolysis of one or more kinds of water and steam.

In a third characteristic configuration of the present invention, a co-electrolysis reaction between water and carbon dioxide is carried out in the electrolytic reaction unit.

According to this characteristic configuration, hydrogen and a certain amount of carbon monoxide can be obtained by decomposing both water and carbon dioxide together in the electrolytic reaction unit. As described above, the co-electrolysis mainly contributes to the donation of hydrogen, but in the hydrocarbon production system according to the present invention, the reverse water-gas shift reaction unit is provided below the electrolytic reaction unit, and thus, a shortage of carbon monoxide can be supplemented by this reverse water-gas shift reaction unit. Further, when the co-electrolysis is performed in the electrolytic reaction unit, the gas flowing in from the electrolytic reaction unit contains water, hydrogen, carbon dioxide, and carbon monoxide, and thus, the reverse water-gas shift reaction can be caused almost as it is.

In a fourth characteristic configuration of the present invention, the reverse water-gas shift reaction unit has a reverse water-gas shift catalyst in which an active metal is supported on a metal oxide carrier.

According to this characteristic configuration, the reverse water-gas shift reaction can be caused by using the catalyst (in the present invention, this catalyst is referred to as a reverse water-gas shift catalyst) in which an active metal is supported on a metal oxide carrier.

As described above, the catalyst in which the active metal is supported on the metal oxide carrier can be easily produced by an operation such as immersing a metal oxide carrier in a solution in which an active metal is dissolved. Therefore, a concentration of the metal oxide carrier and a concentration of the active metal in the catalyst can be satisfactorily controlled, which is preferable.

Here, in order to obtain this kind of catalyst (reverse water-gas shift catalyst), it is preferable to carry out the production through a calcination step of performing calcination at a temperature of 450° C. or higher. It is more preferably 600° C. or higher and 800° C. or higher. This is because this catalyst can advance an equilibrium reaction thereof to the reverse water-gas shift reaction side, which is the object of the present invention, in a high temperature range, and thus, it needs to be used on the high temperature side and further requires high temperature resistance. For example, the catalyst can be used stably even when combined with a solid oxide type electrolytic cell used in a relatively high temperature range (for example, 600° C. to 800° C.). Further, when the calcination temperature is set too high, a cost required for the calcination step becomes too high, and thus, an upper limit is about 1200° C.

Further, when using the catalyst, it is preferable to use catalyst after performing the reduction pretreatment.

As described above, in the catalyst obtained through the calcination step, at least a portion of the catalytically active component is in the state of an oxide, and the activity may not be sufficiently exhibited. Therefore, the reduction pretreatment is performed to reduce the catalytically active component in the oxidized state, and the activity can be sufficiently exerted.

Therefore, regarding the hydrocarbon production system described so far, as an operation method thereof, it is preferable to operate the hydrocarbon production system after applying the reduction pretreatment to the reverse water-gas shift reaction unit. This is a sixteenth characteristic configuration of the present invention.

Further, by applying the catalyst thus obtained (reverse water-gas shift catalyst) to, for example, a surface of a metal support, a reverse water-gas shift reaction can be caused in the gas flowing in contact with the coated surface.

As described in the fourteenth characteristic configuration of the present invention, the hydrocarbon production system having this configuration can be produced by disposing an impregnated supported product, which is obtained through an impregnation-supporting step of impregnating a metal oxide carrier with an active metal to be supported on the metal oxide carrier, at least in the reverse water-gas shift reaction unit.

In a fifth characteristic configuration of the present invention, the reverse water-gas shift catalyst is a reverse water-gas shift catalyst in which at least one or both of nickel and iron are supported as the active metal on a carrier containing a ceria-based metal oxide or a zirconia-based metal oxide as a main component as a metal oxide carrier.

According to this characteristic configuration, by supporting one or both of nickel and iron as the catalytically active component (active metal) on the carrier containing a ceria-based metal oxide or a zirconia-based metal oxide as a main component, as will be described later based on Table 1, Table 2, Table 3, and Table 4, the catalyst is highly active on a relatively high temperature side.

The performance of the catalyst having this configuration showed an activity comparable to that of platinum, which is an expensive precious metal as the catalytically active component.

When one or both of nickel and iron is used as the catalytically active component, a cost per unit weight can be reduced to $\frac{1}{1000}$ or less as compared with platinum, and when the cost is reduced or the same cost is applied, an amount of catalyst used can be increased to each stage, which is preferable.

Further, by using a ceria-based metal oxide or a zirconia-based metal oxide as the carrier, resistance in a high temperature range can be ensured.

In the present invention, the reverse water-gas shift reaction unit is provided on a downstream side (side to which gas generated in electrolytic reaction unit flows) of an electrolytic reaction unit. However, the carrier of the reverse water-gas shift catalyst is formed of the ceria-based metal oxide or the zirconia-based metal oxide, and thus, a thermal expansion coefficient of the reverse water-gas shift catalyst can be made close to that of a material constituting the electrolytic reaction unit, so that the reaction at both units can be satisfactorily generated in almost the same high temperature range.

To obtain this reverse water-gas shift catalyst, by executing at least an impregnation-supporting step of adding a carrier containing a ceria-based metal oxide or a zirconia-based metal oxide as a main component to a solution containing one or both of nickel and iron, and impregnating the carrier with at least one or both of nickel and iron to be supported on the carrier, it is possible to produce the reverse water-gas shift catalyst.

In a sixth characteristic configuration of the present invention, the ceria-based metal oxide is ceria doped with at least one of gadolinium, samarium, and yttrium.

According to this characteristic configuration, the activity as a catalyst can be improved by performing a doping treatment as described later.

In a seventh characteristic configuration of the present invention, the zirconia-based metal oxide is zirconia stabilized by at least one of yttria and scandia.

According to this characteristic configuration, the activity can be improved by a stabilized zirconia catalyst as described later.

In an eighth characteristic configuration of the present invention, in the reverse water-gas shift catalyst described above, copper is supported as the active metal.

According to this characteristic configuration, the activity as the reverse water-gas shift catalyst can be enhanced.

Further, regarding a production method of the hydrocarbon production system, it is preferable to have at least a calcination step of performing the calcination at a temperature of 450° C. or higher in the step of forming the reverse water-gas shift reaction unit. This is a seventeenth characteristic configuration of the present invention.

As will be described later, the reverse water-gas shift catalyst is stored in the reverse water-gas shift reaction unit, but it is preferable that this reverse water-gas shift catalyst is subjected to the calcination treatment in the production process in order to improve stability under high temperature use conditions. The calcination treatment can be performed in the step of forming the reverse water-gas shift reaction unit.

In a ninth characteristic configuration of the present invention, the hydrocarbon synthesis reaction unit has a hydrocarbon synthesis catalyst in which an active metal is supported on a metal oxide carrier.

According to this characteristic configuration, a hydrocarbon synthesis reaction can be caused by using a catalyst (in the present invention, this catalyst is referred to as a hydrocarbon synthesis catalyst) in which an active metal is supported on a metal oxide carrier.

As described above, the catalyst in which the active metal is supported on the metal oxide carrier can be easily produced by an operation such as immersing a metal oxide carrier in a solution in which an active metal is dissolved. Therefore, a concentration of the metal oxide carrier and a concentration of the active metal in the catalyst can be satisfactorily controlled, which is preferable.

Further, by applying the catalyst thus obtained (hydrocarbon synthesis catalyst) to, for example, a surface of a metal support, a hydrocarbon synthesis reverse water reaction can be caused in the gas flowing in contact with the coated surface.

Therefore, as described in the fourteenth characteristic configuration of the present invention, it is also a preferable embodiment to produce the hydrocarbon production system by disposing the impregnated supported product, which is obtained through the impregnation-supporting step of impregnating a metal oxide carrier with an active metal to be supported on the metal oxide carrier, in both the reverse water-gas shift reaction unit and the hydrocarbon synthesis reaction unit.

In a tenth characteristic configuration of the present invention, the active metal is ruthenium.

According to this characteristic configuration, as will be described later, hydrocarbons can be synthesized with high activity.

In an eleventh characteristic configuration of the present invention, the electrolytic (electrolysis) reaction unit has an electrolytic (electrolysis) cell in which at least an electrode layer, an electrolyte layer, and a counter electrode layer are formed on a support.

According to this characteristic configuration, as the electrolytic cell used in the electrolytic reaction unit, for example, the thin-film electrode layer, electrolyte layer, and counter electrode layer are provided on a robust support having sufficient strength even if the support is thin. Therefore, the electrolytic reaction can be effectively caused while reducing the amount of the material used to form these layers to be the electrolytic cell. As a result, it is possible to configure an electrolytic cell unit that is compact, has high performance, and has excellent strength and reliability. Metals and ceramics can be selected as constituent materials of this type of support.

In a twelfth characteristic configuration of the present invention, the support is a metal.

By adopting a metal as the support, a material cost is suppressed by ensuring the strength with an inexpensive metal material, and it is easier to process than ceramics.

In a thirteenth characteristic configuration of the present invention, the hydrocarbon synthesis reaction unit is supported by the support, and the support is a metal.

According to this characteristic configuration, the hydrocarbon synthesis reaction can be effectively caused while reducing the amount of catalyst required for the hydrocarbon synthesis, and the hydrocarbon synthesis unit having excellent heat resistance and durability can be obtained.

Further, by adopting a metal as the support, strength and heat resistance of the hydrocarbon synthesis unit used at a high temperature can be ensured, and stable performance can be exhibited.

BRIEF DESCRIPTION OF THE DRAWINGS

FIGS. 11(*a*)-(*c*) are explanatory diagrams illustrating a preparation state of a catalyst.

FIGS. 12(*a*) and (*b*) are explanatory diagrams illustrating a coating/calcination state and reduction pretreatment of a catalyst.

FIG. 13 is a schematic diagram of an electrolytic cell unit including the electrolytic reaction unit, the reverse water-gas shift reaction unit, and the hydrocarbon synthesis reaction unit.

DESCRIPTION OF THE INVENTION

An embodiment of the present invention will be described with reference to the drawings.

Figure 1:
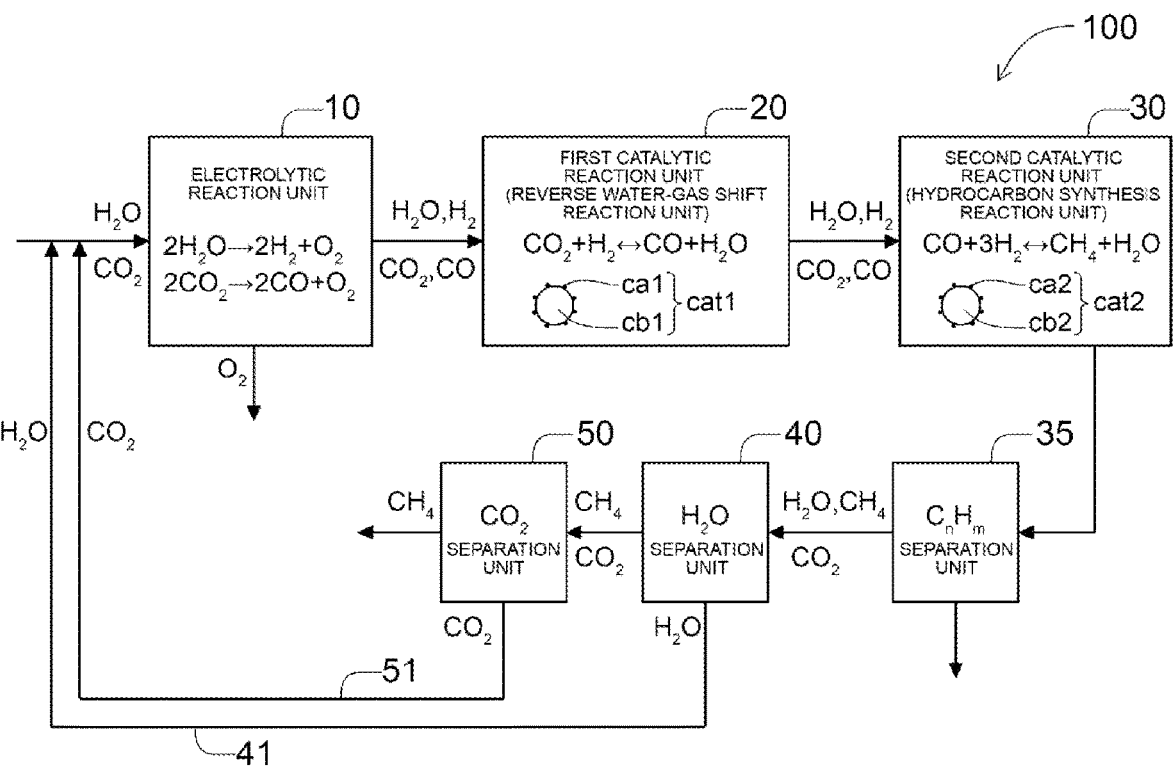
FIG. 1 is a diagram illustrating the configuration of a hydrocarbon production system.

FIG. 1 illustrates a configuration of one form of a hydrocarbon production system 100.

As illustrated in the figure, the hydrocarbon production system 100 includes an electrolytic reaction unit 10, a first catalytic reaction unit 20, a second catalytic reaction unit 30, a heavy hydrocarbon separation unit 35 (illustrated as a CnHm separation unit), a water separation unit 40 (illustrated as an $H_2O$ separation unit), and a carbon dioxide separation unit 50 (illustrated as a $CO_2$ separation unit) in this order.

The electrolytic reaction unit 10 is a unit that electrolyzes at least a portion of an inflowing gas, the first catalytic reaction unit 20 is a reverse water-gas shift reaction unit that carries out a reverse water-gas shift reaction of at least a portion of the inflowing gas, and the second catalytic reaction unit 30 is configured to act as a hydrocarbon synthesis reaction unit that synthesizes at least a portion of the inflowing gas into hydrocarbon. Here, the hydrocarbon synthesized is mainly $CH_4$ (hydrocarbon having one carbon atom), but also includes other lower saturated hydrocarbons having two to four carbon atoms and the like. Further, as will be illustrated later, by appropriately selecting a catalyst used for the second catalytic reaction unit 30, heavy hydrocarbons having a larger number of carbon atoms than the lower saturated hydrocarbons, unsaturated hydrocarbons, oxygen-containing hydrocarbons, or the like can also be synthesized. Therefore, in the present specification, the hydrocarbon is a concept including all of them, and is also collectively referred to as hydrocarbons.

The heavy hydrocarbon separation unit 35, the water separation unit 40, and the carbon dioxide separation unit 50 are units for removing at least a portion of predetermined components (CnHm, $H_2O$, and $CO_2$ in the order of description) from the gas flowing inside. As illustrated in FIG. 1, the components removed and recovered by the water separation unit 40 and the carbon dioxide separation unit 50 are returned to a predetermined unit of the system via a water return path 41 and a carbon dioxide return path 51 and are reused. It is illustrated by $H_2O$ and $CO_2$ returned via both return paths 41 and 51, respectively.

As a result, the hydrocarbon production system 100 is established as a carbon closed system that does not substantially release $CO_2$ to the outside of the system.

In the drawings, the gas flowing into each unit is illustrated in front of each unit, and the gas released from the unit is illustrated after each unit.

In the electrolytic reaction unit 10, $H_2O$ and $CO_2$ as starting materials flow in and are electrolyzed internally, $H_2O$ is decomposed into $H_2$ and $O_2$, and some $CO_2$ is decomposed into CO and $O_2$ and released.

The reaction is described as follows.

$$2H_2O \rightarrow 2H_2 + O_2 \qquad \text{(Formula 1)}$$

$$2CO_2 \rightarrow 2CO + O_2 \qquad \text{(Formula 2)}$$

The formulas 1 and 2 are also illustrated in a box illustrating the electrolytic reaction unit 10 of FIG. 1.

In the first catalytic reaction unit 20 (reverse water-gas shift reaction unit), $H_2$ and $CO_2$ flow in, a reverse water-gas shift reaction occurs inside, $CO_2$ becomes CO, $H_2$ becomes $H_2O$, and CO and $H_2O$ are released.

The reaction is described as the following equilibrium reaction, but the reverse water-gas shift reaction is a reaction (reaction proceeding in a direction in which $CO_2$ and $H_2$ react to generate CO and $H_2O$) in which the reaction described by the following formula 3 proceeds to the right.

$$CO_2 + H_2 \Leftrightarrow CO + H_2O \qquad \text{(Formula 3)}$$

This formula 3 is also illustrated in a box illustrating the first catalytic reaction unit 20 (reverse water-gas shift reaction unit) in FIG. 1. A reverse water-gas shift catalyst cat1 used in the reaction is also schematically illustrated in this box.

In the second catalytic reaction unit 30 (hydrocarbon synthesis reaction unit), $H_2$ and CO flow in, and hydrocarbon is synthesized by a catalytic reaction. For example, the reaction in which $CH_4$ is synthesized from CO and $H_2$ is described as the following equilibrium reaction, but the reaction in which $CH_4$ is synthesized from CO and $H_2$ is a reaction (reaction proceeding in a direction in which CO and $H_2$ react to generate $CH_4$ and $H_2O$) in which the reaction described by the following formula 4 proceeds to the right.

$$CO + 3H_2 \Leftrightarrow CH_4 + H_2O \qquad \text{(Formula 4)}$$

This formula 4 is also illustrated in a box illustrating the second catalytic reaction unit 30 (hydrocarbon synthesis reaction unit) in FIG. 1. A hydrocarbon synthesis catalyst cat2 used in the reaction is also schematically illustrated in this box.

Furthermore, the equilibrium reaction of (Formula 3) also occurs at this unit.

Further, depending on the type of catalyst used in the second catalytic reaction unit 30, it is possible to proceed with a Fischer-Tropsch (FT) synthesis reaction or the like. Therefore, various hydrocarbons such as ethane, propane, butane, pentane, hexane, paraffin, and olefinic hydrocarbons can be synthesized from CO and $H_2$.

As will be described later, the inventors have illustrated an example of a catalyst using ruthenium as a catalytically active component of the hydrocarbon synthesis catalyst cat2 disposed in the second catalytic reaction unit 30, but heavy hydrocarbons are also synthesized in a catalyst containing iron, cobalt, or the like as the catalytically active component, and this type of heavy hydrocarbon can be condensed and separated from a transport gas as the temperature decreases. Therefore, the above-mentioned heavy hydrocarbon separation unit 35 separates the hydrocarbon component separated in this manner.

The generated $H_2O$ is separated in the water separation unit 40 and returned to the upstream side of the electrolytic reaction unit 10 via the water return path 41 (water recycle line).

The generated $CO_2$ is separated in the carbon dioxide separation unit 50 and returned to the upstream side of the electrolytic reaction unit 10 via the carbon dioxide return path 51 (carbon dioxide recycle line).

As a result, in this hydrocarbon production system 100, the hydrocarbon is finally synthesized and can be supplied to the outside.

The above is the outline of the above-mentioned hydrocarbon production system 100, and a configuration of each unit and a role thereof will be described below.

[Electrolytic Reaction Unit]

As illustrated above, the electrolytic reaction unit 10 decomposes $H_2O$ and $CO_2$ that flow in by consuming electric power supplied according to the above formulas 1 and 2.

Figure 2:
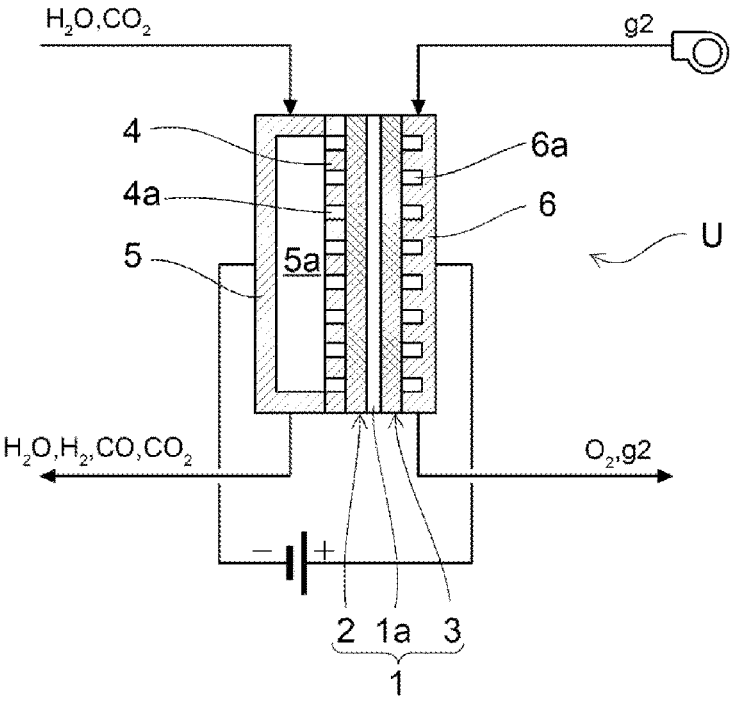
FIG. 2 is a schematic diagram illustrating a configuration of an electrolytic reaction unit.

FIG. 2 schematically illustrates a cross-sectional structure of the electrolytic reaction unit 10.

FIG. 2 illustrates an electrolytic cell unit U which is stacked in multiple to form an electrolytic stack (not illustrated). The electrolytic cell unit U includes an electrolytic cell 1, and the electrolytic cell 1 includes an electrode layer 2 on one surface of an electrolyte layer 1a and a counter electrode layer 3 on the other surface thereof. The electrode layer 2 serves as a cathode in the electrolytic cell 1, and the counter electrode layer 3 serves as an anode. Incidentally, this electrolytic cell unit U is supported by a metal support 4. Here, a case where a solid oxide type electrolytic cell is used as the electrolytic cell 1 is illustrated.

The electrolyte layer 1a can be formed in the state of a thin film having a thickness of 10 μm or less. As a constituent material of the electrolyte layer 1a, YSZ (yttria-stabilized zirconia), SSZ (scandia-stabilized zirconia), GDC (gadolinium-doped ceria), YDC (yttrium-doped ceria), SDC (samarium-doped ceria), and LSGM (strontium/magnesium-added lanthanum gallate), or the like can be used. In particular, zirconia-based ceramics are preferably used.

Preferably, the electrolyte layer 1a is formed by a low-temperature calcination method (for example, a wet method using a calcination treatment in a low temperature range that does not carry out a calcination treatment in a high temperature range exceeding 1100° C.), a spray coating method (thermal spraying method, aerosol deposition method, aerosol gas deposition method, a powder jet deposition method, particle jet deposition method, cold spray method, or the like), a PVD method (sputtering method, a pulse laser deposition method, or the like), a CVD method, or the like. These film forming processes that can be used in a low temperature range provide an electrolyte layer 1a that is dense and has high gastightness and gas barrier properties without using calcination in a high temperature range exceeding, for example, 1100° C. Therefore, damage to the metal support 4 can be suppressed, element mutual diffusion between the metal support 4 and the electrode layer 2 can be suppressed, and an electrolytic cell unit U having excellent performance and durability can be realized. In particular, it is preferable to use the low-temperature calcination method, the spray coating method, or the like because a low-cost element can be realized. Further, it is more preferable to use the spray coating method because the electrolyte layer 1a, which is dense and has high gastightness and gas barrier property, can be easily obtained in a low temperature range.

Further, the electrolyte layer 1a is densely configured in order to prevent the gas leak and exhibit high ionic conductivity. A density of the electrolyte layer 1a is preferably 90% or more, more preferably 95% or more, and further preferably 98% or more. When the electrolyte layer 1a is a uniform layer, the density is preferably 95% or more, and more preferably 98% or more. When the electrolyte layer 1a includes a plurality of layers, it is preferable that at least a portion of the electrolyte layer 1a includes a layer (dense electrolyte layer) having a density of 98% or more, and it is more preferable to include a layer (dense electrolyte layer) having a density of 99% or more. In a case where the dense electrolyte layer is included in a portion of the electrolyte layer 1a, even when the electrolyte layer 1a includes a plurality of layers, it is possible to easily form the electrolyte layer 1a that is dense and has high gastightness and gas barrier property.

The electrode layer 2 can be provided in a thin layer on the front surface of the metal support 4 and in a region larger than a region where holes 4a are provided. In the case of a thin layer, a thickness thereof can be, for example, about 1 μm to 100 μm, preferably 5 μm to 50 μm. With such a thickness, it is possible to secure sufficient electrode performance while reducing the amount of expensive electrode layer material used to reduce costs. The entire region provided with the holes (through holes) 4a is covered with the electrode layer 2. That is, the hole 4a is formed inside the region of the metal support 4 where the electrode layer 2 is formed. In other words, all the holes 4a are provided facing the electrode layer 2.

As the constituent material of the electrode layer 2, for example, a composite material such as NiO-GDC, Ni-GDC, NiO—YSZ, Ni—YSZ, CuO—$CeO_2$, Cu—$CeO_2$ can be used. In these examples, GDC, YSZ, and $CeO_2$ can be referred to as aggregates of the composite material. Preferably, the electrode layer 2 is formed by a low-temperature calcination method (for example, a wet method using a calcination treatment in a low temperature range that does not carry out a calcination treatment in a high temperature range exceeding 1100° C.), a spray coating method (thermal spraying method, aerosol deposition method, aerosol gas deposition method, a powder jet deposition method, particle jet deposition method, cold spray method, or the like), a PVD method (sputtering method, a pulse laser deposition method, or the like), a CVD method, or the like. These processes that can be used in the low temperature range provide an improved electrode layer 2 without using, for example, calcinating in a high temperature range higher than 1100° C. Therefore, the metal support 4 is not damaged, element mutual diffusion between the metal support 4 and the electrode layer 2 can be suppressed, and an electrochemical element having excellent durability can be realized. Further, it is more preferable to use the low-temperature calcination method because the handling of the raw material becomes easy.

The counter electrode layer 3 can be formed in a thin layer on the surface of the electrolyte layer 1a opposite to the electrode layer 2. In the case of a thin layer, a thickness thereof can be, for example, about 1 μm to 100 μm, preferably 5 μm to 50 μm. With such a thickness, it is possible to secure sufficient electrode performance while reducing the amount of expensive counter electrode layer material used to reduce costs. As the material of the counter electrode layer 3, for example, a composite oxide such as LSCF or LSM, a ceria-based oxide, or a mixture thereof can be used. In particular, it is preferable that the counter electrode layer 3 contains a perovskite-type oxide containing two or more kinds of elements selected from the group consisting of La, Sr, Sm, Mn, Co, and Fe.

The electrolyte layer 1a, the electrode layer 2, and the counter electrode layer 3 are formed as a thin film as described later, and the inventor calls this thin layer forming.

As illustrated above, the electrolytic cell unit U has a metal support type, includes a metal support 4 as a support for the electrode layer 2, and a supply path forming member 5 for forming a U-shaped electrode layer-side gas supply path 5a is provided on a side opposite to the electrode layer 2 in a state where the metal support 4 is interposed therebetween. Further, the metal support 4 is provided with a large number of holes 4a penetrating the front and back surfaces. The gas ($H_2O$ and $CO_2$) supplied through the electrode layer-side gas supply path 5a is subject to electrolysis and is supplied to the electrode layer 2 through a large number of holes 4a. Further, the generated gas ($H_2$, CO) is discharged from the hole 4a.

Meanwhile, also on the counter electrode layer 3 side, a supply path forming member 6 for forming a counter electrode layer-side gas supply path 6a is provided. As illustrated in FIG. 2, the supply path forming member 6 is provided with many grooves on the counter electrode layer 3 side and is configured to supply a transport gas g2 (for example, air) to the counter electrode layer-side gas supply path 6a.

The metal support 4 supports the electrode layer 2, the electrolyte layer 1a, and the counter electrode layer 3 and serves as a support for maintaining the strength of the electrolytic cell 1 and the electrolytic cell unit U as a whole. In this example, the plate-shaped metal support 4 is used as the metal support, but other shapes such as a box shape and a cylindrical shape are also possible.

The metal support 4 may have sufficient strength to form the electrolytic cell unit U as a support, and for example, can use a support having a thickness of about 0.1 mm to 2 mm, preferably about 0.1 mm to 1 mm, and more preferably about 0.1 mm to 0.5 mm. In the present embodiment, the support is made of metal, but ceramics can also be used, for example.

The metal support 4 has, for example, the plurality of holes 4a provided so as to penetrate the front surface and the back surface of the metal plate. For example, the hole 4a can be provided in the metal support 4 by mechanical, chemical, or optical drilling. The hole 4a has a function of allowing gas to pass from the back surface to the front surface of the metal support 4. The hole 4a may be provided so as to be inclined in a gas flow direction (the front and back directions of the paper surface in FIG. 2).

By using a ferrite-based stainless steel material (an example of an Fe—Cr-based alloy) as a material of a base material of the metal support 4, a thermal expansion coefficient of the metal support 4 can be made close to those of YSZ (yttria-stabilized zirconia), GDC (gadolinium-doped ceria, also referred to as CGO), and the like used as materials for the electrode layer 2 and the electrolyte layer 1a. Therefore, the electrolytic cell unit U is less likely to be damaged even when the low temperature and high temperature cycles are repeated. Therefore, it is preferable because the electrolytic cell unit U having excellent long-term durability can be realized.

The same material as that of the metal support 4 can be used for the supply path forming members 5 and 6 of the electrolytic cell unit U, and the thickness thereof can be substantially the same.

Although the metal support 4 and both supply path forming members 5 and 6 have conductivity, they are gastightly configured to function as a separator for separating the supply paths 5a and 6a.

In the electrolytic cell unit U having the above configuration, in an electrolysis operation, DC power is supplied between the pair of electrode layers 2 and 3 provided with the electrolyte layer 1a interposed therebetween from a power supply unit (illustrated by a battery in FIG. 2). In the present embodiment, as illustrated in FIG. 2, the case where the electrode layer 2 side is negative and the counter electrode layer 3 side is positive is illustrated. Depending on the configuration of the electrolytic cell unit U, the electrode layer 2 side may be positive and the counter electrode layer 3 side may be negative.

Then, $H_2O$ and $CO_2$, which are gases to be electrolyzed, are supplied to the electrode layer 2 from an electrolytic raw material supply unit (upstream portion of the electrolytic reaction unit 10 in FIG. 1), and the transport gas g2 is supplied to the counter electrode layer side. Therefore, the reactions illustrated in the formulas 1 and 2 can be caused in the electrolytic cell 1 and the decomposed gas can be taken out. Here, regarding the supply of $H_2O$, either water or steam may be used, or both of them may be used. Therefore, in the present invention, an electrolytic cell device is constructed which includes at least the electrolytic cell unit U, the electrolytic raw material supply unit that supplies water and/or steam and carbon dioxide to the electrolytic cell unit U, and the power supply unit that supplies electric power.

The supplied gas ($H_2O$, $CO_2$) and the released gas ($H_2O$, $H_2$, CO, $O_2$, $CO_2$) in the electrolytic reaction are illustrated above and below the electrolytic cell unit U in FIG. 2. However, this is for ease of understanding, and in fact, the above-mentioned electrode layer-side gas supply path 5a and counter electrode layer-side gas supply path 6a are formed so as to extend in the front and back directions of the paper surface of FIG. 2, and for example, the gas ($H_2O$, $CO_2$) on the supply side described on an upper side of the electrolytic cell unit U in FIG. 2 can be recovered from the front side of the paper surface, and the gas ($H_2O$, $H_2$, CO, $O_2$, $CO_2$) on the release side described on the lower side of the electrolytic cell 1 can be recovered from the back side of the paper surface (refer to FIG. 4 described later). In addition, in order to smoothly perform the discharge of $O_2$ generated in the electrolytic reaction, for example, the transport gas g2 such as air can flow through the electrolytic cell unit U.

When $H_2O$ and $CO_2$ are supplied to the electrolytic reaction unit 10 to carry out the electrolysis, $H_2O$ has a lower electrolytic voltage than $CO_2$ and is easily electrolyzed. Therefore, when $H_2O$ and $CO_2$ having the same amount are temporarily supplied to the electrolytic reaction unit 10 and the electrolytic reaction is carried out, the $H_2$ concentration tends to be higher than the CO concentration at the outlet of the electrolytic reaction unit 10, and unreacted $CO_2$ tends to remain.

[First Catalytic Reaction Unit (Reverse Water-Gas Shift Reaction Unit)]

As illustrated above, the first catalytic reaction unit 20 (reverse water-gas shift reaction unit) causes a reverse water-gas shift reaction, converts $CO_2$ into CO using the supplied $H_2$, and converts $H_2$ into $H_2O$. That is, in the electrolytic reaction unit 10 that supplies $H_2O$ and $CO_2$ to electrolyze, the remaining $CO_2$ that is not decomposed is converted into CO.

The reaction here is as illustrated by the formula 3, but this reaction is an endothermic reaction and is an equilibrium reaction according to the reaction temperature conditions. As a result, as described above, it is preferable that the catalyst is capable of causing the reaction represented by the formula 3 on the high temperature side (for example, 600° C. to 800° C.) as much as possible.

In the description of the catalyst in the present specification, a component having activity as a catalyst may be referred to as a "catalytically active component", and a carrying body carrying the catalytically active component may be referred to as a "carrier (catalyst support)".

The inventors examined various combinations of catalytically active components and carriers as described later, and found that a specific combination was suitable.

In a production of this type of catalyst, by executing an impregnation-supporting step of immersing the carrier (metal oxide carrier) in a solution containing a catalytically active component (active metal), taking out the carrier, drying and heat-treating the carrier, it is possible to easily obtain a carrier-support catalyst (impregnated supported product) in which the catalytically active component is distributed on the surface of the carrier. This heat treatment is a calcination treatment. The preparation and use of the catalyst will be described with reference to FIGS. 11(a)-(c) and FIGS. 12(a) and (b).

A preparation method described here is the same except that the starting material is different in the combination of various catalytically active components and carriers. FIGS. 11(a)-(c) illustrate examples of the reverse water-gas shift catalyst cat1 and the hydrocarbon synthesis catalyst cat2 according to the present invention. In FIGS. 11(a)-(c), the catalytically active component of the reverse water-gas shift catalyst cat1 is referred to as ca1, and the carrier thereof is referred to as cb1. Meanwhile, regarding the hydrocarbon synthesis catalyst cat2, the catalytically active component thereof is ca2 and the carrier thereof is cb2.

As illustrated in FIGS. 11(a)-(c), in the catalyst preparation, after an impregnation-supporting step (a) of obtaining an aqueous solution of a compound containing a metal component (which is a metal catalyst) to be the catalytically active components ca1 and ca2, inputting the carriers cb1 and cb2 into the aqueous solution, and carrying out stirring and impregnation is executed, a drying/crushing/molding step (b) of carrying out evaporative drying, drying, and crushing and molding is executed, and thereafter, a calcination step (c) of calcination an obtained molded product in the air is executed, and thus, the target product (cat1, cat2) can be obtained. Therefore, this form of catalyst is also referred to as an impregnation-supported catalyst.

In this case, as illustrated in the example of the reverse water-gas shift catalyst cat1 in FIGS. 12(a) and (b), the catalyst can be applied to a portion where the catalyst is used and calcined. FIG. 12(a) illustrates a coating/calcination step in which the reverse water-gas shift catalyst cat1 is applied to the metal support 4 in which the holes 4a are perforated to form a coating layer 20a, and the coating layer 20a is calcined. FIG. 12(b) illustrates a reduction pretreatment step in which H$_2$ flows to carry out a reduction pretreatment before using the reverse water-gas shift catalyst cat1.

When the calcination treatment is carried out in air, the supported catalytically active components ca1 and ca2 are in a state where a part or all of them are oxidized. Before using the catalyst, a so-called reduction pretreatment may be carried out to reduce the catalytically active component in an oxidized state to sufficiently enhance the activity. FIG. 12(b)

illustrates a state in which a reducing gas (typically H$_2$) is circulated on the surface of the catalyst to carry out the reduction pretreatment.

(Catalyst Used)

As the reverse water-gas shift catalyst cat1 used for the first catalytic reaction unit 20, the inventors have selected a catalyst that satisfies the following requirements.

A catalyst composed by supporting at least one or both of nickel and iron as the catalytically active component ca1 on the carrier cb1 containing a ceria-based metal oxide or a zirconia-based metal oxide as a main component. Here, since the strength of the catalyst cat1 can be increased, a ratio of the carrier cb1 to the entire catalyst is preferably 55% by weight or more, more preferably 60% by weight or more, and further preferably 65% by weight or more. Further, an upper limit of this ratio can be, for example, 99.5% by weight, but when the upper limit is more than this, the catalytically active component ca1 cannot be sufficiently supported, and it may be difficult to obtain the effect as the reverse water-gas shift catalyst cat1.

Further, as the ceria-based metal oxide, ceria doped with at least one of gadolinium, samarium, and yttrium can also be used.

Further, as the zirconia-based metal oxide, zirconia stabilized by at least one of yttria and scandia can also be used.

Since the reverse water-gas shift reaction can proceed satisfactorily, a supported amount of the catalytically active component ca1 is preferably 0.5% by weight or more, more preferably 1% by weight or more, and further preferably 5% by weight or more. Further, when the supported amount of the catalytically active component ca1 is increased too much, it becomes difficult to support the catalytically active component ca1 in a high dispersion, it is difficult to obtain a significant improvement in the catalytic activity, and the catalyst cost also increases. Accordingly, the supported amount of the catalytically active component ca1 is preferably 35% by weight or less, more preferably 30% by weight or less, and further preferably 25% by weight or less.

Further, it is also preferable to add either one or both of nickel and iron to the catalytically active component ca1 to support copper as a further catalytically active component ca1. In this configuration, the supported amount of copper is equal to or less than the supported amount of the catalytically active component ca1 with either one or both of nickel and iron as a main catalytically active component ca1.

Hereinafter, test results of Examples in the case where the catalytically active component ca1 and the carrier cb1 are variously changed as the reverse water-gas shift catalyst cat1 used for the first catalytic reaction unit 20 will be described.

As the catalytically active component ca1, Ni and Fe were examined and compared with Pt (platinum).

As the carrier cb1, Al$_2$O$_3$ (alumina) was also examined using ZrO$_2$ (zirconia), YSZ (yttria-stabilized zirconia), GDC (gadolinium-doped ceria), and CeO$_2$ (ceria) as examples.

In the following description, Test 1 and Test 2 will be introduced, but a difference between the two tests is that in the calcination of the reverse water-gas shift catalyst cat1, the calcination temperature of Test 1 is set to 450° C., and the calcination temperature of Test 2 is set to a high temperature side of 600° C. to 1000° C.

(Test 1)

The test results of Examples (1 to 19) when the carrier is variously changed as the catalyst used for the first catalytic reaction unit 20 will be described.

As catalytically active components, Ni and Fe were examined, and were compared with Pt (platinum).

As the carrier, $ZrO_2$ (zirconia), YSZ (yttria-stabilized zirconia), GDC (gadolinium-doped ceria), and $CeO_2$ (ceria) were used as examples, and $Al_2O_3$ (alumina) was also examined.

(Catalyst Preparation)

In preparing the reverse water-gas shift catalyst cat1, an aqueous solution is obtained by quantifying and dissolving out in a generally used temperature range, but in Test 1, the catalysts of the following examples were each at 80° C., 80° C., and 450° C.

Table 1 illustrates Examples 1 to 19 of the reverse water-gas shift catalyst cat1 in the present invention.

A horizontal axis represents the type of carrier cb1, a metal supported amount (% by weight; expressed as wt. % in the table) as the catalytically active component, a CO adsorption amount (ml/g), and a BET surface area $(m^2/g)$.

Regarding the CO adsorption amount, the CO adsorption amount was measured after the catalyst was subjected to a reduction pretreatment at 350° C. for 1 hour under a hydrogen atmosphere.

TABLE 1

| | Catalyst | Carrier | Metal supported amount (wt. %) | CO adsorption amount (Nml/g) | BET surface area $(m^2/g)$ |
|---|---|---|---|---|---|
| Example 1 | $Ni/ZrO_2$ | $ZrO_2$ | Ni: 9.5 | 1.48 | 11.1 |
| Example 2 | Ni/8YSZ | 8YSZ | Ni: 9.5 | 1.97 | 11.3 |
| Example 3 | Ni/GDC | GDC | Ni: 9.1 | 3.61 | 14.3 |
| Example 4 | $Ni/CeO_2$ | $CeO_2$ | Ni: 14 | 0.47 | 9.4 |
| Example 5 | $Ni—Fe/CeO_2$ | $CeO_2$ | Ni: 9.1 Fe: 0.46 | 0.45 | 8.9 |
| Example 6 | $Ni—Cu/CeO_2$ | $CeO_2$ | Ni: 9.2 Cu: 0.49 | 0.78 | 10.6 |
| Example 7 | $Ni/Al_2O_3$ | $Al_2O_3$ | Ni: 8.9 | 0.65 | 90.7 |
| Example 8 | $Fe/ZrO_2$ | $ZrO_2$ | Fe: 9.6 | 0.88 | 12.0 |
| Example 9 | Fe/8YSZ | 8YSZ | Fe: 9.5 | 0.22 | 7.5 |
| Example 10 | Fe/GDC | GDC | Fe: 9.2 | 0.30 | 15.2 |
| Example 11 | $Fe/CeO_2$ | $CeO_2$ | Fe: 9.3 | 0.53 | 10.3 |
| Example 12 | $Fe—Ni/ZrO_2$ | $ZrO_2$ | Fe: 9.7 Ni: 0.49 | 0.52 | 13.0 |
| Example 13 | $Fe—Cu/ZrO_2$ | $ZrO_2$ | Fe: 9.7 Cu: 0.50 | 0.21 | 10.5 |
| Example 14 | $Fe/Al_2O_3$ | $Al_2O_3$ | Fe: 8.8 | 0.31 | 82.8 |
| Example 15 | $Pt/ZrO_2$ | $ZrO_2$ | Pt: 0.95 | 0.95 | 11.2 |
| Example 16 | Pt/8YSZ | 8YSZ | Pt: 0.92 | 1.18 | 4.8 |
| Example 17 | Pt/GDC | GDC | Pt: 0.96 | 1.10 | 10.0 |
| Example 18 | $Pt/CeO_2$ | $CeO_2$ | Pt: 0.95 | 1.17 | 7.9 |
| Example 19 | $Pt/Al_2O_3$ | $Al_2O_3$ | Pt: 0.95 | 1.85 | 97.8 | any one or both of a water-soluble nickel compound (nickel nitrate, nickel chloride, nickel sulfate, nickel ammonium sulfate, nickel acetate, nickel oxalate, nickel citrate, or the like) and a water-soluble iron compound (iron nitrate, iron chloride, iron sulfate, ammonium iron sulfate, iron acetate, iron oxalate, iron citrate, or the like) according to the composition of the target catalyst. Further, when supporting copper as another catalytically active component ca1, an aqueous solution is obtained by similarly quantifying and dissolving a water-soluble copper compound (copper nitrate, copper chloride, copper sulfate, ammonium copper sulfate, copper acetate, copper oxalate, copper citrate, or the like). A predetermined amount of carrier powder (ceria, zirconia, GDC, YSZ, $Al_2O_3$) is added to the aqueous solution, stirred and impregnated, then evaporated to dryness, dried, then crushed and molded, and then calcinated in air. This impregnation is the "impregnation-supporting step" referred to in the present invention, and the result is the "impregnated supported product".

The catalysts of the following examples were prepared using nickel nitrate hexahydrate, iron nitrate nonahydrate, and copper nitrate trihydrate, respectively. The catalyst using Pt was prepared using tetraamine platinum hydroxide.

In the above catalyst preparation, temperatures of evaporation to dryness, drying, and calcination could be carried (Catalytic Activity Test)

In the catalytic activity test, a mixed gas of 50% $H_2$-50% $CO_2$ (a mixed gas containing $H_2$ and $CO_2$ in a ratio of 1:1 (volume ratio)) was used as a reaction gas, and the reaction temperature was changed from 600° C. to 800° C. in increments of 50° C. under the conditions in which a Gas Hourly Space Velocity (GHSV) was 10000/h.

Before conducting the catalytic activity test, the reduction pretreatment of the catalyst was carried out at 600° C. while flowing a hydrogen gas through the catalyst layer.

As the test results, a $CO_2$ conversion rate (%), a CO concentration (%) at the outlet of the reaction unit, and a $CH_4$ concentration (%) are illustrated in Table 2.

The $CO_2$ conversion rate (%) was calculated according to the following formula based on a gas analysis result at the outlet of the catalyst layer.

$$[CH_4 \text{ concentration}]+[CO \text{ concentration}]/([CH_4 \text{ concentration}]+[CO \text{ concentration}]+[CO_2 \text{ concentration}])$$

As illustrated above, in the reverse water-gas shift catalyst cat1 used in the first catalytic reaction unit 20 (reverse water-gas shift reaction unit), it is desirable that the $CO_2$ conversion rate (%) on the high temperature side (for example, around 600 to 800° C.) is high.

TABLE 2

| | Catalyst | | Reaction temperature (° C.) | | | | |
|---|---|---|---|---|---|---|---|
| | | | 600 | 650 | 700 | 750 | 800 |
| Example 1 | Ni/ZrO$_2$ | CO$_2$ conversion rate (%) | 31.8 | 37.6 | 41.6 | 44.0 | 46.1 |
| | | Outlet CO concentration (%) | 17.9 | 23.1 | 25.8 | 28.0 | 29.7 |
| | | Outlet CH$_4$ concentration (%) | 3.7 | 0.9 | 0.3 | 0.1 | 0.1 |
| Example 2 | Ni/8YSZ | CO$_2$ conversion rate (%) | 32.7 | 36.4 | 37.5 | 39.3 | 40.7 |
| | | Outlet CO concentration (%) | 16.9 | 21.1 | 22.7 | 23.7 | 24.8 |
| | | Outlet CH$_4$ concentration (%) | 4.0 | 1.3 | 0.6 | 0.4 | 0.2 |
| Example 3 | Ni/GDC | CO$_2$ conversion rate (%) | 29.9 | 33.8 | 36.2 | 38.5 | 39.6 |
| | | Outlet CO concentration (%) | 14.3 | 18.8 | 21.1 | 22.8 | 24.3 |
| | | Outlet CH$_4$ concentration (%) | 5.1 | 2.0 | 0.9 | 0.4 | 0.2 |
| Example 4 | Ni/CeO$_2$ | CO$_2$ conversion rate (%) | 34.5 | 38.9 | 41.9 | 44.7 | 47.4 |
| | | Outlet CO concentration (%) | 18.4 | 23.3 | 25.8 | 27.9 | 30.2 |
| | | Outlet CH$_4$ concentration (%) | 3.4 | 0.8 | 0.2 | 0.1 | 0.0 |
| Example 5 | Ni—Fe/CeO$_2$ | CO$_2$ conversion rate (%) | 34.1 | 40.0 | 42.0 | 45.6 | 47.7 |
| | | Outlet CO concentration (%) | 18.6 | 23.6 | 27.3 | 29.0 | 30.5 |
| | | Outlet CH$_4$ concentration (%) | 3.4 | 0.8 | 0.2 | 0.1 | 0.0 |
| Example 6 | Ni—Cu/CeO$_2$ | CO$_2$ conversion rate (%) | 35.2 | 41.0 | 44.2 | 46.9 | 48.6 |
| | | Outlet CO concentration (%) | 19.2 | 24.4 | 27.3 | 29.1 | 31.0 |
| | | Outlet CH$_4$ concentration (%) | 3.3 | 0.8 | 0.2 | 0.1 | 0.0 |
| Example 7 | Ni/Al$_2$O$_3$ | CO$_2$ conversion rate (%) | 28.5 | 33.6 | 35.9 | 37.4 | 39.5 |
| | | Outlet CO concentration (%) | 15.4 | 19.3 | 21.6 | 23.2 | 23.9 |
| | | Outlet CH$_4$ concentration (%) | 4.6 | 1.8 | 0.8 | 0.6 | 0.4 |
| Example 8 | Fe/ZrO$_2$ | CO$_2$ conversion rate (%) | 39.7 | 42.3 | 45.1 | 47.5 | 49.6 |
| | | Outlet CO concentration (%) | 23.0 | 25.4 | 27.2 | 29.3 | 31.2 |
| | | Outlet CH$_4$ concentration (%) | 0.0 | 0.0 | 0.0 | 0.0 | 0.0 |
| Example 9 | Fe/8YSZ | CO$_2$ conversion rate (%) | 36.3 | 40.4 | 43.1 | 45.9 | 47.5 |
| | | Outlet CO concentration (%) | 22.5 | 25.4 | 27.6 | 29.3 | 31.2 |
| | | Outlet CH$_4$ concentration (%) | 0.0 | 0.0 | 0.0 | 0.0 | 0.0 |
| Example 10 | Fe/GDC | CO$_2$ conversion rate (%) | 35.8 | 40.2 | 42.5 | 44.6 | 46.8 |
| | | Outlet CO concentration (%) | 21.9 | 25.2 | 27.0 | 28.6 | 30.4 |
| | | Outlet CH$_4$ concentration (%) | 0.0 | 0.0 | 0.0 | 0.0 | 0.0 |
| Example 11 | Fe/CeO$_2$ | CO$_2$ conversion rate (%) | 37.2 | 40.9 | 43.5 | 45.4 | 48.3 |
| | | Outlet CO concentration (%) | 22.9 | 25.3 | 27.6 | 29.6 | 31.4 |
| | | Outlet CH$_4$ concentration (%) | 0.0 | 0.0 | 0.0 | 0.0 | 0.0 |
| Example 12 | Fe—Ni/ZrO$_2$ | CO$_2$ conversion rate (%) | 38.1 | 41.6 | 44.0 | 46.8 | 48.3 |
| | | Outlet CO concentration (%) | 23.3 | 25.4 | 27.6 | 29.6 | 31.5 |
| | | Outlet CH$_4$ concentration (%) | 0.1 | 0.0 | 0.0 | 0.0 | 0.0 |
| Example 13 | Ni—Cu/CeO$_2$ | CO$_2$ conversion rate (%) | 36.5 | 41.3 | 45.1 | 47.3 | 49.2 |
| | | Outlet CO concentration (%) | 22.9 | 25.3 | 27.5 | 29.6 | 31.4 |
| | | Outlet CH$_4$ concentration (%) | 0.3 | 0.1 | 0.0 | 0.0 | 0.0 |
| Example 14 | Fe/Al$_2$O$_3$ | CO$_2$ conversion rate (%) | 22.5 | 27.6 | 33.7 | 40.0 | 45.0 |
| | | Outlet CO concentration (%) | 12.7 | 15.8 | 20.1 | 24.5 | 28.6 |
| | | Outlet CH$_4$ concentration (%) | 0.1 | 0.0 | 0.0 | 0.0 | 0.0 |
| Example 15 | Pt/ZrO$_2$ | CO$_2$ conversion rate (%) | 34.0 | 39.8 | 43.0 | 45.7 | 48.2 |
| | | Outlet CO concentration (%) | 19.0 | 24.4 | 27.0 | 29.2 | 31.3 |
| | | Outlet CH$_4$ concentration (%) | 3.2 | 0.7 | 0.2 | 0.1 | 0.0 |
| Example 16 | Pt/8YSZ | CO$_2$ conversion rate (%) | 35.1 | 40.7 | 44.1 | 46.4 | 48.8 |
| | | Outlet CO concentration (%) | 19.3 | 24.5 | 27.3 | 29.4 | 31.3 |
| | | Outlet CH$_4$ concentration (%) | 3.2 | 0.7 | 0.2 | 0.1 | 0.0 |
| Example 17 | Pt/GDC | CO$_2$ conversion rate (%) | 32.9 | 38.6 | 42.5 | 45.2 | 47.8 |
| | | Outlet CO concentration (%) | 18.6 | 23.5 | 26.4 | 28.8 | 30.6 |
| | | Outlet CH$_4$ concentration (%) | 3.3 | 0.8 | 0.2 | 0.1 | 0.0 |
| Example 18 | Pt/CeO$_2$ | CO$_2$ conversion rate (%) | 34.9 | 39.4 | 43.1 | 45.6 | 48.3 |
| | | Outlet CO concentration (%) | 19.7 | 24.1 | 26.5 | 29.4 | 31.4 |
| | | Outlet CH$_4$ concentration (%) | 2.7 | 0.8 | 0.2 | 0.1 | 0.0 |
| Example 19 | Pt/Al$_2$O$_3$ | CO$_2$ conversion rate (%) | 35.5 | 41.1 | 44.7 | 47.5 | 49.6 |
| | | Outlet CO concentration (%) | 19.4 | 24.6 | 27.6 | 29.7 | 31.2 |
| | | Outlet CH$_4$ concentration (%) | 3.2 | 0.8 | 0.2 | 0.1 | 0.0 |

60

(Test 2)

Hereinafter, the test results of Examples (20 to 29) of Test 2 will be described. Even in this Test, Ni and Fe were examined as catalytically active components, and the addition of Cu was also examined.

As the carrier, CeO$_2$ (ceria) and ZrO$_2$ (zirconia) are used as examples, and Al$_2$O$_3$ (alumina) is also examined.

(Catalyst Preparation)

The reverse water-gas shift catalyst cat1 used in Test 2 was prepared in the same manner as in Test 1 except that the calcination temperatures were changed to 600° C., 800° C., and 1000° C.

Table 3 illustrates the catalyst of each of Examples (20 to 29) prepared.

TABLE 3

|  | Catalyst | Carrier | Calcination temperature (° C.) | CO adsorption amount (Nml/g) | BET surface area (m²/g) |
|---|---|---|---|---|---|
| Example 20 | Ni/CeO$_2$ | CeO$_2$ | 600 | 0.9 | 8.9 |
| Example 21 | Ni—Cu/CeO$_2$ | CeO$_2$ | 600 | 0.53 | 9.1 |
| Example 22 | Fe/ZrO$_2$ | ZrO$_2$ | 600 | 0.27 | 13.4 |
| Example 23 | Fe/Al$_2$O$_3$ | Al$_2$O$_3$ | 600 | 0.15 | 96.0 |
| Example 24 | Ni/CeO$_2$ | CeO$_2$ | 800 | 0.26 | 7.6 |
| Example 25 | Ni—Cu/CeO$_2$ | CeO$_2$ | 800 | 0.51 | 7.6 |
| Example 26 | Fe/ZrO$_2$ | ZrO$_2$ | 800 | 0.16 | 10.1 |
| Example 27 | Fe/Al$_2$O$_3$ | Al$_2$O$_3$ | 800 | 0.14 | 83.5 |
| Example 28 | Ni/CeO$_2$ | CeO$_2$ | 1000 | 0.08 | 5.2 |
| Example 29 | Fe/ZrO$_2$ | ZrO$_2$ | 1000 | 0.29 | 8.1 |

(Catalytic Activity Test)

In the catalytic activity test, a mixed gas containing H$_2$ and CO$_2$ in a ratio of 1:1 (volume ratio) was used as a reaction gas, and the reaction temperature was changed from 600° C. to 800° C. in increments of 50° C. under the conditions in which GHSV was 10000/h.

Before conducting the catalytic activity test, the reduction pretreatment of the catalyst was carried out at 600° C. while flowing a hydrogen gas through the catalyst layer.

As the test results, the CO$_2$ conversion rate (%), the CO concentration (%) at the outlet of the reaction unit, and the CH$_4$ concentration (%) are illustrated in Table 4.

For reference, an equilibrium value (calculated value) of the CO$_2$ conversion rate under the experimental conditions is illustrated in Table 4.

Iron/Zirconia Catalyst and Iron/Alumina Catalyst

For the iron/zirconia catalyst, the test results when the calcination temperatures are 450° C., 600° C., 800° C., and 1000° C. are illustrated in Example 8, Example 22, Example 26, and Example 29, respectively. Meanwhile, for the iron/alumina catalyst, the test results when the calcination temperatures are 450° C., 600° C., and 800° C. are illustrated in Example 14, Example 23, and Example 27, respectively. As can be seen from these results, although the metal supported

TABLE 4

|  | Catalyst |  | Reaction temperature (° C.) | | | | |
|---|---|---|---|---|---|---|---|
|  |  |  | 600 | 650 | 700 | 750 | 800 |
| Example 20 | Ni/CeO$_2$ | CO$_2$ conversion rate (%) | 33.8 | 39.5 | 42.8 | 45.7 | 48.1 |
|  |  | Outlet CO concentration (%) | 18.8 | 24.2 | 27.4 | 29.6 | 31.4 |
|  |  | Outlet CH$_4$ concentration (%) | 3.3 | 0.8 | 0.2 | 0.0 | 0.0 |
| Example 21 | Ni—Cu/CeO$_2$ | CO$_2$ conversion rate (%) | 34.7 | 40.4 | 42.9 | 44.6 | 46.7 |
|  |  | Outlet CO concentration (%) | 19.1 | 24.4 | 27.0 | 28.6 | 29.9 |
|  |  | Outlet CH$_4$ concentration (%) | 3.7 | 0.9 | 0.2 | 0.1 | 0.0 |
| Example 22 | Fe/ZrO$_2$ | CO$_2$ conversion rate (%) | 38.1 | 40.4 | 43.1 | 45.7 | 48.2 |
|  |  | Outlet CO concentration (%) | 23.3 | 25.8 | 28.0 | 30.2 | 31.8 |
|  |  | Outlet CH$_4$ concentration (%) | 0.0 | 0.0 | 0.0 | 0.0 | 0.0 |
| Example 23 | Fe/Al$_2$O$_3$ | CO$_2$ conversion rate (%) | 24.8 | 29.0 | 35.3 | 40.6 | 45.3 |
|  |  | Outlet CO concentration (%) | 14.0 | 16.8 | 20.8 | 25.3 | 29.5 |
|  |  | Outlet CH$_4$ concentration (%) | 0.0 | 0.0 | 0.0 | 0.0 | 0.0 |
| Example 24 | Ni/CeO$_2$ | CO$_2$ conversion rate (%) | 33.9 | 39.2 | 42.7 | 45.6 | 47.1 |
|  |  | Outlet CO concentration (%) | 19.2 | 24.6 | 27.4 | 29.5 | 31.7 |
|  |  | Outlet CH$_4$ concentration (%) | 3.3 | 0.7 | 0.2 | 0.0 | 0.0 |
| Example 25 | Ni—Cu/CeO$_2$ | CO$_2$ conversion rate (%) | 34.2 | 39.3 | 41.9 | 44.3 | 46.6 |
|  |  | Outlet CO concentration (%) | 18.5 | 23.9 | 26.0 | 28.7 | 30.7 |
|  |  | Outlet CH$_4$ concentration (%) | 3.6 | 0.9 | 0.1 | 0.1 | 0.0 |
| Example 26 | Fe/ZrO$_2$ | CO$_2$ conversion rate (%) | 38.1 | 41.2 | 43.7 | 46.2 | 48.4 |
|  |  | Outlet CO concentration (%) | 23.5 | 25.7 | 28.1 | 30.0 | 31.9 |
|  |  | Outlet CH$_4$ concentration (%) | 0.0 | 0.0 | 0.0 | 0.0 | 0.0 |
| Example 27 | Fe/Al$_2$O$_3$ | CO$_2$ conversion rate (%) | 22.2 | 25.2 | 32.7 | 38.9 | 43.9 |
|  |  | Outlet CO concentration (%) | 13.4 | 15.1 | 20.0 | 24.5 | 29.1 |
|  |  | Outlet CH$_4$ concentration (%) | 0.0 | 0.0 | 0.0 | 0.0 | 0.0 |
| Example 28 | Ni/CeO$_2$ | CO$_2$ conversion rate (%) | 34.5 | 40.6 | 44.5 | 46.3 | 48.7 |
|  |  | Outlet CO concentration (%) | 19.1 | 24.6 | 28.6 | 30.4 | 31.8 |
|  |  | Outlet CH$_4$ concentration (%) | 3.5 | 0.8 | 0.2 | 0.1 | 0.0 |
| Example 29 | Fe/ZrO$_2$ | CO$_2$ conversion rate (%) | 37.8 | 41.2 | 44.5 | 46.0 | 48.1 |
|  |  | Outlet CO concentration (%) | 22.6 | 25.5 | 27.6 | 29.5 | 31.3 |
|  |  | Outlet CH$_4$ concentration (%) | 0.0 | 0.0 | 0.0 | 0.0 | 0.0 |
| Reference (equilibrium value) |  | CO$_2$ conversion rate (%) | 34.6 | 39.9 | 43.6 | 46.4 | 49.0 | amount is slightly different, the iron/zirconia catalyst is superior to the iron/alumina catalyst in the activity in carrying out the reverse water-gas shift reaction. Further, the iron/zirconia catalyst has extremely high catalytic activity not only when the calcination temperature is 450° C. but also when the calcination temperature is as high as 600° C., 800° C., and 1000° C., and regardless of the calcination temperature, the $CO_2$ conversion rate of the iron/zirconia catalyst reaches the vicinity of the equilibrium value.

Nickel/Ceria Catalyst

The test results when the calcination temperatures are 450° C., 600° C., 800° C., and 1000° C. are illustrated in Example 4, Example 20, Example 24, and Example 28, respectively. As can be seen from these results, the nickel/ceria catalyst has extremely high catalytic activity not only when the calcination temperature is 450° C. but also when the calcination temperature is as high as 600° C., 800° C., and 1000° C., and regardless of the calcination temperature, the $CO_2$ conversion rate of nickel/ceria catalyst reaches the vicinity of the equilibrium value.

Nickel/Alumina Catalyst

Example 7 illustrates the test results when the calcination temperature is 450° C. As a result, the nickel/alumina catalyst had a lower $CO_2$ conversion rate than the nickel/ceria catalyst described above.

Nickel/Copper/Ceria Catalyst

The test results when the calcination temperatures are 450° C., 600° C., and 800° C. are illustrated in Example 6, Example 21, and Example 25, respectively. From these results, it can be seen that the $CO_2$ conversion rate of the nickel/copper/ceria catalysts tends to decrease slightly when the calcination temperature thereof is as high as 600° C. or 800° C., but the calcination temperature conditions described above are superior to those of the similar iron/alumina catalyst. Further, in the nickel/copper/ceria catalyst having the calcination temperature of 450° C., the $CO_2$ conversion rate reaches the vicinity of the equilibrium value.

Usefulness as Reverse Water-Gas Shift Catalyst

As illustrated above, the iron/zirconia-based catalysts and the nickel/ceria-based catalysts exhibit extremely high reverse water-gas shift catalytic activity even when the calcination temperature is variously changed to 450° C. to 1000° C., and thus, for example, even when used in combination with a solid oxide type electrolytic cell used in a high temperature range of around 600° C. to 800° C., it is easy to secure high performance and durability, which is useful.

From the above results, as illustrated above, as the reverse water-gas shift catalyst cat1 used for the first catalytic reaction unit 20, the catalyst obtained by supporting at least one or both of nickel and iron as the catalytically active component ca1 on the carrier cb1 containing the ceria-based metal oxide or the zirconia-based metal oxide as a main component can be used.

Further, as the ceria-based metal oxide as the carrier cb1, ceria doped with at least one of gadolinium, samarium, and yttrium can also be used.

Further, the zirconia-based metal oxide as the carrier cb1 can be zirconia stabilized by at least one of yttria and scandia.

Further, it is also preferable to add either one or both of nickel and iron to the catalytically active component ca1 to support copper as a further catalytically active component ca1.

By using the reverse water-gas shift catalyst cat1 in the first catalytic reaction unit 20 (reverse water-gas shift reaction unit), the reverse water-gas shift reaction can be carried out at around 600 to 1000° C. with the $CO_2$ conversion rate (%) equal to or higher than that of the Pt catalyst, which is highly active but very expensive.

Since the test of this example was carried out under a very high GHSV condition of 10000/h, by reducing the GHSV to less than 10000/h, that is, by increasing the amount of catalyst used with respect to the amount of gas to be treated, it is possible to carry out the reverse water-gas shift reaction at a higher $CO_2$ conversion rate (%).

[Combination of Electrolytic Reaction Unit and Reverse Water-Gas Shift Reaction Unit]

In the description so far, according to the system configuration illustrated in FIG. 1, the electrolytic reaction unit 10 and the reverse water-gas shift reaction unit 20 are individually provided in the order described along the flow direction of the gas.

Figure 3:
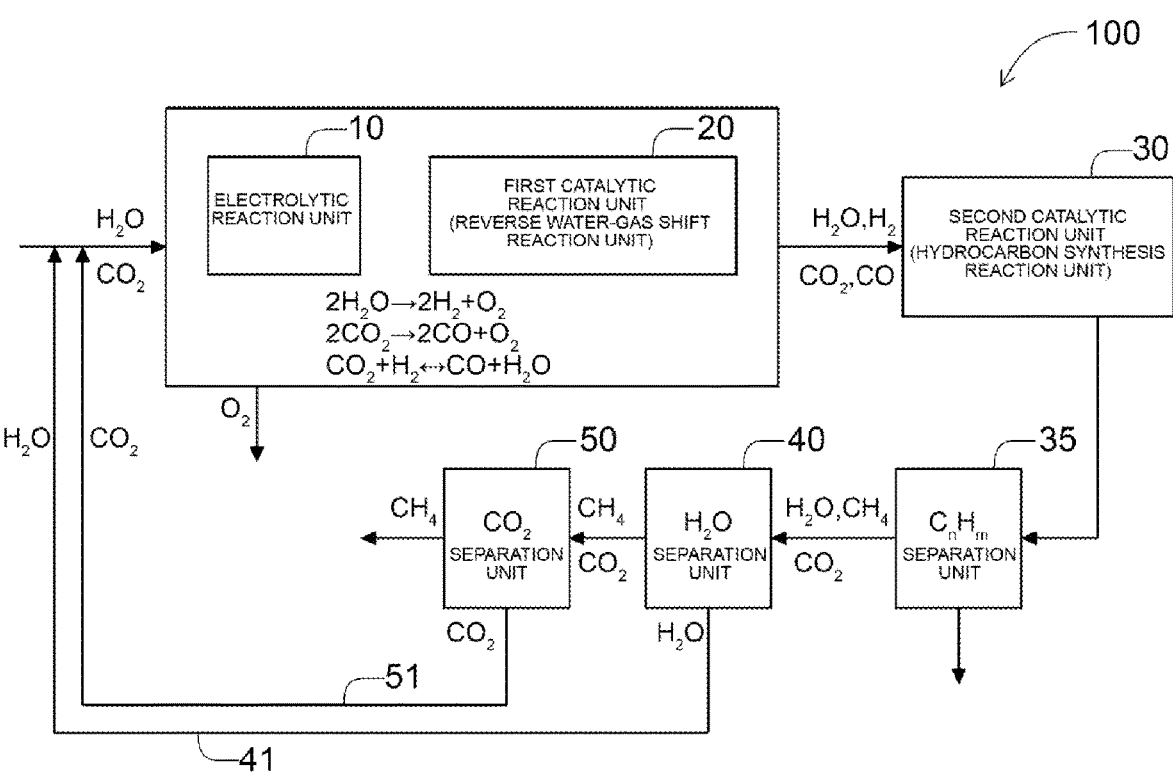
FIG. 3 is a diagram illustrating the configuration of a system in which the electrolytic reaction unit and a reverse water-gas shift reaction unit are integrated.

The reaction of the electrolytic reaction unit 10 is an exothermic reaction depending on the reaction conditions, and the reaction of the reverse water-gas shift reaction unit 20 is an endothermic reaction. Therefore, thermal efficiency of the system can be improved by integrating the two reaction units 10 and 20. In this way, FIG. 3 illustrates a configuration in which the two reaction units 10 and 20 are combined and integrated, and the integration is illustrated to surround both units. In addition, a reaction when integrated in the same box in this way is illustrated. Basically, the above-mentioned formulas 1, 2, and 3 are carried out. In a case where the electrolytic reaction unit 10 and the reverse water-gas shift reaction unit 20 are combined and integrated, preferably, when the units are surrounded together by a heat insulating member, heat can be efficiently transferred between the electrolytic reaction unit 10 and the reverse water-gas shift reaction unit 20. Further, in order to transfer the heat generated in the electrolytic reaction unit 10 to the reverse water-gas shift reaction unit 20, the electrolytic reaction unit 10 and the reverse water-gas shift reaction unit 20 may be connected using a heat transfer member.

[Electrolytic Cell Unit Equipped with Both Electrolytic Reaction Unit and Reverse Water-Gas Shift Reaction Unit]

Based on the above concept, it is preferable to provide the reverse water-gas shift reaction unit 20 in the electrolytic cell unit U which is the electrolytic reaction unit 10. This is because when a solid oxide type electrolytic cell that operates at around 600 to 800° C. is used as the electrolytic cell 1, in the reverse water-gas shift catalyst cat1 of the present application which can obtain high activity at around 600 to 800° C., the electrolytic reaction unit 10 and the reverse water-gas shift reaction unit 20 can be used in the same temperature range.

In this case as well, it is sufficient that the gas that has passed through the electrolytic reaction unit 10 is guided to the reverse water-gas shift reaction unit 20 to generate the reverse water-gas shift reaction.

Figure 4:
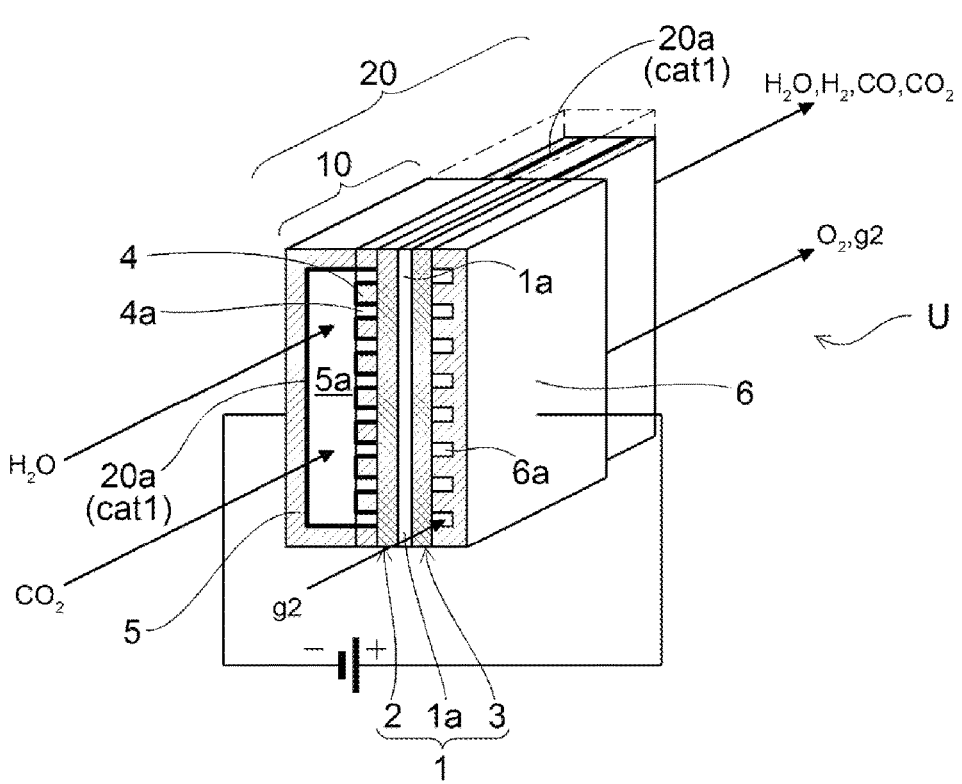
FIG. 4 is a schematic diagram of an electrolytic cell unit including the electrolytic reaction unit and the reverse water-gas shift reaction unit.

FIG. 4 illustrates an electrolytic cell unit U provided with such a reverse water-gas shift reaction unit 20. FIG. 4 is a diagram illustrating the electrolytic cell unit U illustrated in cross section in FIG. 2 including the flow direction of the gas.

As illustrated in FIG. 4, the cross sections of the electrolytic cell unit U are basically the same.

That is, the electrolytic cell unit U also includes the electrolytic cell 1 in which the electrode layer 2 and the counter electrode layer 3 are formed with the electrolyte layer 1a interposed therebetween, the metal support 4 which functions as a support thereof and also acts as a separator, and the supply path forming members 5 and 6, and the electrode layer-side gas supply path 5a and the counter electrode layer-side gas supply path 6a are formed in the electrolytic cell unit U. More specifically, as can be seen from FIG. 4, when the metal support 4 is viewed in the flow direction of gas, the holes 4a are provided in the portion corresponding to the electrolytic cell 1, but the hole is not provided on the downstream side of the electrode layer 2. Therefore, the metal support 4 is a separator which effectively separates the gas which is supplied to the electrode layer 2 and released from the electrode layer 2, and the gas which is supplied to the counter electrode layer 3 gas and is released from the counter electrode layer 3.

However, in this example, the reverse water-gas shift catalyst cat1 described above is applied to an inner surface (supply path-side inner surface of supply path forming member 5, surface of the metal support 4 opposite to surface on which electrode layer 2 is formed, and surfaces of the plurality of holes 4a) of the electrode layer-side gas supply path 5a. A coating layer 20a is illustrated by a thick solid line.

Further, the electrode layer-side gas supply path 5a extends beyond the electrolytic reaction unit 10, and the coating layer 20a is also provided on the extension side.

As a result, the electrode layer-side gas supply path 5a of the electrolytic cell unit U is a discharge path for discharging at least $H_2$ generated in the electrode layer 2, and the electrolytic cell unit U is integrally provided with the electrolytic reaction unit 10 and the reverse water-gas shift reaction unit 20.

In this configuration, the metal support 4 acts as a separator that separates $H_2$ generated in the electrode layer 2 and $O_2$ generated in the counter electrode layer 3, and at least a portion of the separator on the discharge path side of $H_2$ is reverse water-gas shift reaction unit 20.

By stacking the electrolytic cell units U configured in this way in a right-left direction of FIGS. 2 and 4, a large number of electrolytic cell units U are stacked, and it is possible to form a so-called electrolytic cell module (not illustrated) in which the electrolytic cell units are electrically connected to each other. Of course, a useful gas generated can be obtained over multiple layers.

The inventors have stored a granular reverse water-gas shift catalyst cat1 in the electrode layer-side gas supply path 5a and conducted an experiment under a concept in which the electrolytic reaction unit 10 and the reverse water-gas shift reaction unit 20 are combined with each other (the electrode layer-side gas supply path 5a of the electrolytic reaction unit 10 is the reverse water-gas shift reaction unit 20).

Figure 5:
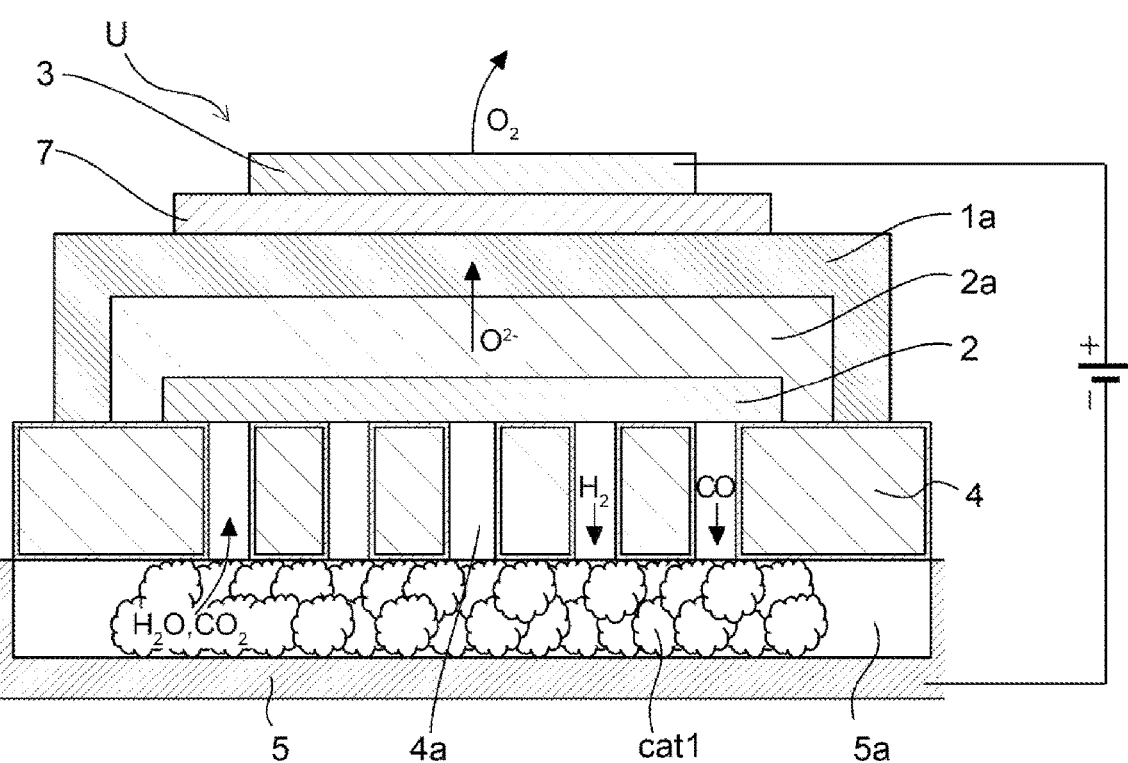
FIG. 5 is a cross-sectional view of an electrolytic cell unit used in a comparative experiment in which an electrode layer-side gas supply path is used as the reverse water-gas shift reaction unit.

FIG. 5 illustrates a cross section of the electrolytic cell unit U used in this experiment.

Hereinafter, a specific description will be given with reference to FIG. 5. FIG. 5 illustrates a cross-sectional view of the electrolytic cell unit U.

Here, as the electrolytic cell 1, a metal-supported solid oxide type electrolytic cell was used. As the metal support 4, a metal substrate was prepared by providing a plurality of through holes (which become holes 4a) by applying laser processing to a ferritic stainless steel metal plate having a thickness of 0.3 mm. The electrode layer 2 and an intermediate layer 2a were laminated in this order on the metal substrate, and the electrolyte layer 1a was laminated on the intermediate layer 2a of the metal substrate so as to cover the intermediate layer 2a. Further, a reaction prevention layer 7 and the counter electrode layer 3 were sequentially laminated on the electrolyte layer 1a to prepare the electrolytic cell 1. A mixture of NiO powder and GDC powder was used as the material for forming the electrode layer 2, GDC powder was used as the material for forming the intermediate layer 2a, 8YSZ (8 µmol % yttria-stabilized zirconia) powder was used as the material for forming the electrolyte layer 1a, GDC powder was used as the material for forming the reaction prevention layer 7, and a mixture of and GDC powder and LSCF powder was used as the material for forming the counter electrode layer 3. Further, the thicknesses of the electrode layer 2, the intermediate layer 2a, the electrolyte layer 1a, the reaction prevention layer 7, and the counter electrode layer 3 were about 25 µm, about 10 µm, about 5 µm, about 5 µm, and about 20 µm, respectively. By providing the intermediate layer 2a between the electrode layer 2 and the electrolyte layer 1a and providing the reaction prevention layer 7 between the electrolyte layer 1a and the counter electrode layer 3, the performance and durability of the electrolytic cell 1 can be improved. Moreover, preferably, the intermediate layer 2a and the reaction prevention layer 7 are formed by a low-temperature calcination method (for example, a wet method using a calcination treatment in a low temperature range that does not carry out a calcination treatment in a high temperature range exceeding 1100° C.), a spray coating method (thermal spraying method, aerosol deposition method, aerosol gas deposition method, a powder jet deposition method, particle jet deposition method, cold spray method, or the like), a PVD method (sputtering method, a pulse laser deposition method, or the like), a CVD method, or the like. These processes that can be used in the low temperature range provide the improved intermediate layer 2a and reaction prevention layer 7 without using, for example, calcinating in a high temperature range higher than 1100° C. Therefore, it is preferable because the electrolytic cell 1 having excellent performance and durability can be realized without damaging the metal support 4. Further, it is more preferable to use the low-temperature calcination method because the handling of the raw material becomes easy.

Regarding the electrolytic cell unit U obtained as described above, the performance improvement in the case where the reverse water-gas shift catalyst cat1 formed in the form of particles was stored in the electrode layer-side gas supply path 5a (which also serves as the discharge path of the gas electrolyzed by the electrolytic reaction unit 10) was examined.

Results when reverse water-gas shift catalyst cat1 is not stored

An electrolytic reaction was carried out while supplying a gas containing $H_2O$ and $CO_2$ to the electrolytic cell unit U, and a ratio of $H_2$ to CO of an outlet gas of the electrolytic cell unit U was measured using a gas chromatograph. The results are illustrated in Table 5 below. The experimental results are described as Comparative Examples A1 and A2.

TABLE 5

| | Inlet gas | Electrolytic voltage (V) | Reaction temperature (° C.) | Ratio of $H_2$/CO of outlet gas |
|---|---|---|---|---|
| Comparative Example A1 | 52%$H_2O$—13%$CO_2$—$N_2$ balance | 1.2 | 700 | 14.2 |

TABLE 5-continued

|  | Inlet gas | Electrolytic voltage (V) | Reaction temperature (° C.) | Ratio of $H_2$/ CO of outlet gas |
|---|---|---|---|---|
| Comparative Example A2 | 49%$H_2O$—17%$CO_2$—$N_2$ balance | 1.2 | 700 | 9.9 |

Results when the reverse water-gas shift catalyst cat1 is stored

As the reverse water-gas shift catalyst cat1, a granular catalyst obtained by supporting about 10% of Ni on the 8YSZ carrier similar to in Example 2 was stored, an electrolytic reaction was carried out while supplying a gas containing $H_2O$ and $CO_2$ to the electrolytic cell unit U, and the ratio of $H_2$ to CO of the outlet gas of the electrolytic cell unit U was measured using a gas chromatograph. The results are illustrated in Table 6. The experimental result is described as Example A1.

TABLE 6

|  | Inlet gas | Electrolytic voltage (V) | Reaction temperature (° C.) | Ratio of $H_2$/ CO of outlet gas |
|---|---|---|---|---|
| Example A1 | 51%$H_2O$—16%$CO_2$—$N_2$ balance | 1.15 | 700 | 5.4 |

By the above comparative experiment, in the electrolytic cell unit U in which the electrolytic cell 1 was formed in a thin layer on the metal support 4, and the reverse water-gas shift reaction unit 20 generating CO by using $CO_2$ and $H_2$ by the reverse water-gas shift reaction was provided in the electrode layer-side gas supply path 5a which was the discharge path of the electrolyzed gas, it was possible to increase a composition ratio of CO to $H_2$ generated by electrolysis.

In the comparison between the electrolytic cell unit U in which the reverse water-gas shift catalyst cat1 is not stored in the electrode layer-side gas supply path 5a (which is the discharge path for the electrolyzed gas) and the electrolytic cell unit U in which the reverse water-gas shift catalyst cat1 is stored, the hydrogen/carbon monoxide ([$H_2$/CO]) ratio changes from about 10 or more to about 5 at the outlet, and by combining the reaction of the electrolytic reaction unit 10 and the reaction of the reverse water-gas shift reaction unit 20, the amount of CO that is advantageous for various hydrocarbon syntheses can be secured, which is preferable. In addition, since thermal efficiency of the hydrocarbon production system 100 can be improved by adopting a methanation reaction of CO rather than a methanation reaction of $CO_2$, by combining the reaction of the electrolytic reaction unit 10 and the reaction of the reverse water-gas shift reaction unit 20, the amount of CO can be secured, which is preferable. This is because 2 µmol of $H_2O$ is generated when 1 µmol of $CO_2$ is methanized, whereas 1 µmol of $H_2O$ is generated when 1 µmol of CO is methanized, and thus, the hydrocarbon production system 100 that employs the methanation reaction of CO can suppress latent heat and sensible heat loss of 1 µmol of $H_2O$ as a whole system.

By appropriately adjusting the ratio of $H_2O$ and $CO_2$ introduced into the electrolytic reaction unit 10, the reaction conditions (electrolytic voltage, reaction temperature, or the like) of the electrolytic reaction unit 10, the reaction conditions (amount of catalyst used, GHSV, reaction temperature, or the like) of the reverse water-gas shift reaction unit 20, or the like, the hydrogen/carbon monoxide ([$H_2$/CO]) ratio at the outlet of the reverse water-gas shift reaction unit 20 can be adjusted to a value (for example, $H_2$/CO=3 which is the equivalent ratio of the methanation reaction of CO, or the like) suitable for the second catalytic reaction unit 30 (hydrocarbon synthesis reaction unit) in the subsequent stage.

[Install Heat Exchanger between Electrolytic Reaction Unit and Reverse Water-Gas Shift Reaction Unit]

Figure 6:
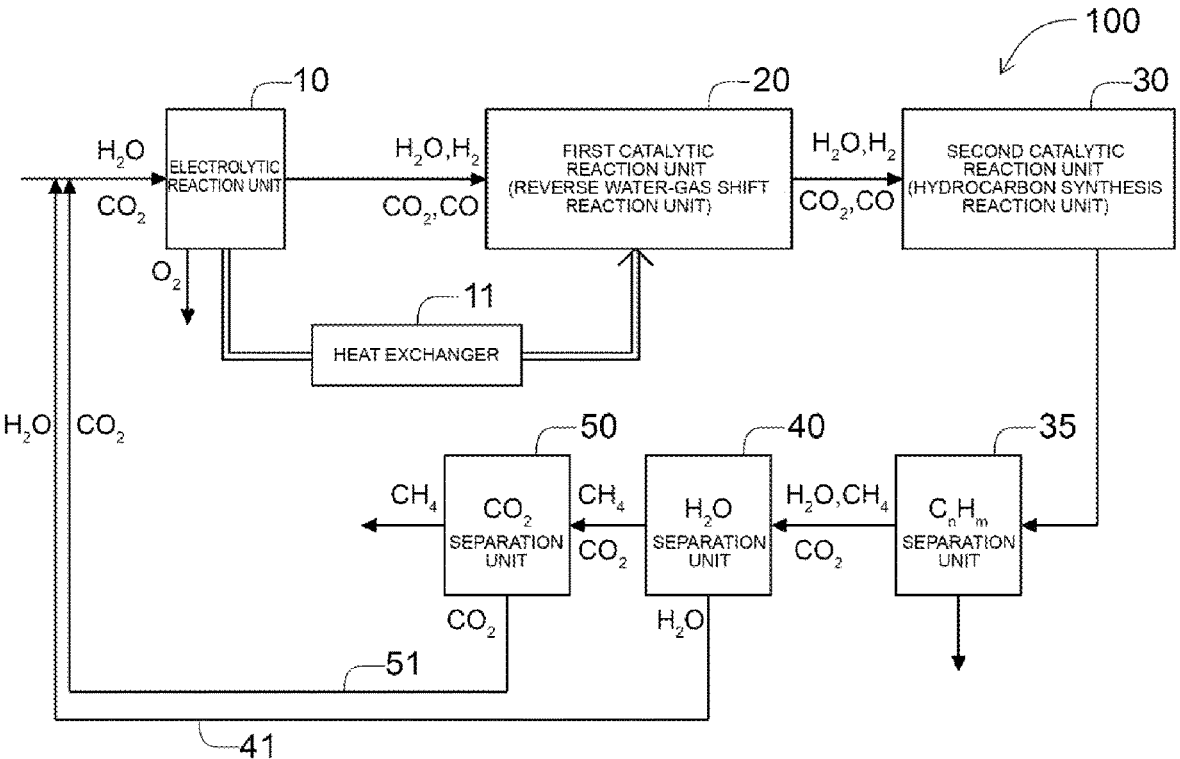
FIG. 6 is a configuration diagram of a system equipped with a heat exchanger between the electrolytic reaction unit and the reverse water-gas shift reaction unit.

In the descriptions so far, the example in which the electrolytic reaction unit 10 and the first catalytic reaction unit (reverse water-gas shift reaction unit) 20 are integrated has been mainly described, however, it is possible to adopt a configuration in which both units 10 and 20 are set as separate units and a heat exchanger 11 is provided between both units 10 and 20 so that heat can be exchanged between both units. This configuration is illustrated in FIG. 6 corresponding to FIG. 1. A hollow double line illustrates the heat transfer between both units. In this configuration, the temperature of each of the units 10 and 20 can be appropriately controlled.

The inventors have called the system including the electrolytic reaction unit 10 and the reverse water-gas shift reaction unit 20 described so far as an "electrolytic reaction system".

[Second Catalytic Reaction Unit (Hydrocarbon Synthesis Reaction Unit)]

At least $H_2$ and CO flow into the second catalytic reaction unit 30 (hydrocarbon synthesis reaction unit), and hydrocarbons (methane and various hydrocarbons having two or more carbon atoms) and the like are generated by the catalytic reaction.

(Example of Hydrocarbon Synthesis Catalyst)

As an activity test of the catalyst (hydrocarbon synthesis catalyst cat2) used in the second catalytic reaction unit 30, the inventors conducted the following evaluation test 1, evaluation test 2, and evaluation test 3.

As an example of the hydrocarbon synthesis catalyst cat2, a catalyst was prepared by variously changing the carrier and the catalytically active component. As the catalytically active component ca2, those obtained by adding Mo, V, Fe, Co, and the like to Ru and Ru, and Ni were examined. As the carrier cb2, $ZrO_2$, $Al_2O_3$, $SiO_2$, MgO, and $TiO_2$ were examined.

(Catalyst Preparation)

The preparation of the hydrocarbon synthesis catalyst cat2 is also the method adopted as described with reference to FIGS. 11(a)-(c) and FIGS. 12(a) and (b).

That is, a water-soluble ruthenium compound (ruthenium nitrate, ruthenium chloride, ruthenium sulfate, ruthenium ammonium sulfate, ruthenium acetate, ruthenium oxalate, ruthenium citrate, or the like) is quantified and dissolved according to the composition of the target catalyst to obtain an aqueous solution. Further, when molybdenum, vanadium, iron, and cobalt are supported as further catalytically active components, these water-soluble metal compounds are similarly quantified to obtain a dissolved aqueous solution. Using the aqueous solution, for example, by impregnating and supporting the catalytically active component on carrier particles ($ZrO_2$, $Al_2O_3$, $SiO_2$, MgO, $TiO_2$) having a predetermined amount, and carrying out necessary treatment steps such as a drying treatment, a calcination treatment, and a reduction treatment, the hydrocarbon synthesis catalyst cat2 can be obtained.

Using ruthenium chloride aqueous solution, ammonium molybdate aqueous solution, vanadyl oxalate aqueous solution, iron nitrate aqueous solution, and cobalt nitrate aqueous solution, respectively, and when both ruthenium and catalytically active components other than ruthenium are supported, the catalysts of the following examples were prepared using a sequential carrier method (a two-step carrier method in which a catalytically active component other than ruthenium is first supported on a carrier and then ruthenium is supported).

$$\text{CO}_2 \text{ removal assumed hydrocarbon conversion rate} = \frac{[\text{number of carbons in hydrocarbons in outlet gas}]}{[\text{number of carbons in outlet gas} - \text{number of carbons in outlet CO}_2]} \qquad 1.$$

This indicator is an indicator illustrating the conversion rate to hydrocarbons when $CO_2$ is removed from the outlet gas of the hydrocarbon synthesis reaction unit 30 obtained by the catalytic reaction, and it is preferable that this indicator is high.

$$\text{C1-C4 calorific value (MJ/Nm}^3) = \Sigma(\text{Nn} \times \text{HN})/\Sigma\text{Nn} \qquad 2.$$

Nn [mol]: number of moles of Cn hydrocarbon in gas of catalytic reaction unit (n=1 to 4)

HN [MJ/m$^3$(N)]: calorific value of Cn hydrocarbon in gas of catalytic reaction unit

[H1=39.8, H2=69.7, H3=99.1, H4=128.5]

This indicator is an indicator illustrating amounts of C1 to C4 components contained in the outlet gas of the hydrocarbon synthesis reaction unit 30 obtained by the catalytic reaction, and when this value exceeds 39.8, it can be confirmed that hydrocarbons such as ethane, propane, and butane are generated in addition to methane.

Regarding the evaluation test 1, Tables 7 and 8 illustrated below illustrate Examples B1 to B3 of the hydrocarbon synthesis catalyst cat2 in the present invention.

TABLE 7

| | Catalyst | Carrier | Active component supported amount (wt. %) | BET surface area (m$^2$/g) | CO adsorption amount (ml/g) |
|---|---|---|---|---|---|
| Example B1 | Ru/Al$_2$O$_3$ | Al$_2$O$_3$ | Ru: 0.4 | 87.4 | 0.66 |
| Example B2 | Ru/Mo/Al$_2$O$_3$ | Al$_2$O$_3$ | Ru: 0.6, Mo: 0.7 | 88.2 | 1.06 |
| Example B3 | Ru/V/Al$_2$O$_3$ | Al$_2$O$_3$ | Ru: 0.7, V: 1.2 | 91.1 | 1.20 |

TABLE 8

| | Catalyst | Indicator | Reaction temperature (° C.) | | | |
|---|---|---|---|---|---|---|
| | | | 275 | 310 | 335 | 360 |
| Example B1 | Ru/Al$_2$O$_3$ | CO$_2$ removal assumed hydrocarbon conversion rate (%) | 12.4 | | | 100.0 |
| | | C$_1$-C$_4$ calorific value (MJ/Nm$^3$) | 44.9 | | | 39.8 |
| Example B2 | Ru/Mo/Al$_2$O$_3$ | CO$_2$ removal assumed hydrocarbon conversion rate (%) | | | 99.8 | |
| | | C$_1$-C$_4$ calorific value (MJ/Nm$^3$) | | | 39.9 | |
| Example B3 | Ru/V/Al$_2$O$_3$ | CO$_2$ removal assumed hydrocarbon conversion rate (%) | | 90.0 | | |
| | | C$_1$-C$_4$ calorific value (MJ/Nm$^3$) | | 42.1 | | |

(Evaluation Test 1)

In the evaluation test 1, a mixed gas containing 12.4% CO, 24.8% $CO_2$, 37.2% $H_2$, 12.4% $H_2O$ and the balance being $N_2$ was used as the reaction gas, GHSV was set to 4000/h (WET base), and the activity test of the hydrocarbon synthesis catalyst cat2 was carried out at a reaction temperature of 275° C. to 360° C. In this case, the reaction gas is an example obtained by assuming a model in which a co-electrolysis reaction between water and carbon dioxide in the electrolytic reaction unit 10 is carried out under the conditions that an electrolytic reaction rate of carbon dioxide is low, and a mixed gas of CO, $CO_2$, $H_2$, and $H_2O$ after the reverse water-gas shift reaction of carbon dioxide is carried out in the reverse water-gas shift reaction unit 20 installed in the subsequent stage is introduced into the hydrocarbon synthesis reaction unit 30 to carry out the hydrocarbon synthesis reaction.

The following two indicators were adopted when organizing the test results.

As illustrated in Tables 7 and 8, it was confirmed that hydrocarbons could be synthesized using a catalyst in which ruthenium was supported on an alumina carrier or a catalyst in which molybdenum or vanadium was supported in addition to ruthenium as a hydrocarbon synthesis catalyst cat2 from the mixed gas of CO, $CO_2$, $H_2$, and $H_2O$.

From the above results, it was confirmed that the above-mentioned hydrocarbon production system 100 could generate a high-calorie gas having a C1-C4 calorific value of 39 MJ/Nm$^3$ or more.

(Evaluation Test 2) In the evaluation test 2, a mixed gas containing 0.45% CO, 18.0% $CO_2$, 71.55% $H_2$, and 10.0% $H_2O$ was used as the reaction gas, GHSV was set to 5000/h (DRY base), and the activity test of the hydrocarbon synthesis catalyst cat2 was carried out at a reaction temperature of about 230° C. to about 330° C. In this case, the reaction gas is an example obtained by assuming a model in which the mixed gas obtained when the co-electrolysis reaction of water and carbon dioxide is carried out in the electrolytic reaction unit 10 under the conditions that the electrolytic reaction rate of carbon dioxide is low is introduced into the hydrocarbon synthesis reaction unit 30 to carry out a hydrocarbon synthesis reaction.

The following two indicators were adopted when organizing the test results.

> hydrocarbon conversion rate=[number of carbons in
> hydrocarbons in outlet gas]/[number of carbons
> in outlet gas]                     1.

This indicator is an indicator illustrating the ratio of the number of carbons converted into hydrocarbons without being converted into $CO_2$ among the total carbons flowing in, and it is preferable that this indicator is high.

> $CO_2$ removal assumed hydrocarbon conversion rate=
> [number of carbons in hydrocarbons in outlet
> gas]/[number of carbons in outlet gas−number
> of carbons in outlet $CO_2$]                     2.

This indicator is an indicator illustrating the conversion rate to hydrocarbons when $CO_2$ is removed from the outlet gas of the hydrocarbon synthesis reaction unit obtained by the catalytic reaction, and it is preferable that this indicator is also high.

For the evaluation test 2, the used catalysts (Examples B4 to B16) are illustrated in Table 9, and the test results are illustrated in Table 10.

TABLE 9

|  | Catalyst | Carrier | Active component supported amount (wt. %) | BET surface area (m²/g) | CO adsorption amount (ml/g) |
|---|---|---|---|---|---|
| Example B4 | Ru/Al₂O₃ | Al₂O₃ | Ru: 1.3 | 109.8 | 0.47 |
| Example B5 | Ru/SiO₂ | SiO₂ | Ru: 1.0 | 212.3 | 0.13 |
| Example B6 | Ru/MgO | MgO | Ru: 1.3 | 24.7 | 0.15 |
| Example B7 | Ru/TiO₂ | TiO₂ | Ru: 1.2 | 64.7 | 0.71 |
| Example B8 | Ru/Al₂O₃ | Al₂O₃ | Ru: 2.3 | 114.5 | 0.97 |
| Example B9 | Ru/Mo/Al₂O₃ | Al₂O₃ | Ru: 1.4, Mo: 1.5 | 131.4 | 0.47 |
| Example B10 | Ru/V/Al₂O₃ | Al₂O₃ | Ru: 1.2, V: 2.1 | 108.3 | 0.45 |
| Example B11 | Ru/Mo/Al₂O₃ | Al₂O₃ | Ru: 2.5, Mo: 1.7 | 115.5 | 1.24 |
| Example B12 | Ru/V/ZrO₂ | ZrO₂ | Ru: 1.1, V: 1.4 | 46.4 | 0.62 |
| Example B13 | Ru/V/Al₂O₃ | Al₂O₃ | Ru: 1.2, V: 3.9 | 118.0 | 0.63 |
| Example B14 | Ru/V/TiO₂ | TiO₂ | Ru: 1.2, V: 1.4 | 57.2 | 1.19 |
| Example B15 | Ru/Mo/TiO₂ | TiO₂ | Ru: 1.2, Mo: 1.2 | 58.1 | 1.21 |
| Example B16 | Ni/Al₂O₃ | Al₂O₃ | Ni: 13.0 | 95.7 | 0.01 |

TABLE 10

|  | Catalyst | Indicator | Reaction temperature (° C.) | | | | | | | |
|---|---|---|---|---|---|---|---|---|---|---|
|  |  |  | 233 | 249 | 257 | 273 | 274 | 276 | 277 | 278 |
| Example B4 | Ru/Al₂O₃ | Hydrocarbon conversion rate (%) |  |  |  |  |  |  |  |  |
|  |  | CO₂ removal assumed hydrocarbon conversion rate (%) |  |  |  |  |  |  |  |  |
| Example B5 | Ru/SiO₂ | Hydrocarbon conversion rate (%) |  |  |  |  |  |  |  |  |
|  |  | CO₂ removal assumed hydrocarbon conversion rate (%) |  |  |  |  |  |  |  |  |
| Example B6 | Ru/MgO | Hydrocarbon conversion rate (%) |  |  |  |  |  |  |  | 4.2 |
|  |  | CO₂ removal assumed hydrocarbon conversion rate (%) |  |  |  |  |  |  |  | 78.0 |
| Example B7 | Ru/TiO₂ | Hydrocarbon conversion rate (%) |  |  |  |  |  | 64.2 |  |  |
|  |  | CO₂ removal assumed hydrocarbon conversion rate (%) |  |  |  |  |  | 99.9 |  |  |
| Example B8 | Ru/Al₂O₃ | Hydrocarbon conversion rate (%) |  |  |  |  |  |  |  |  |
|  |  | CO₂ removal assumed hydrocarbon conversion rate (%) |  |  |  |  |  |  |  |  |
| Example B9 | Ru/Mo/Al₂O₃ | Hydrocarbon conversion rate (%) | 14.2 |  |  | 74.6 |  |  |  |  |
|  |  | CO₂ removal assumed hydrocarbon conversion rate (%) | 99.8 |  |  | 100.0 |  |  |  |  |
| Example B10 | Ru/V/Al₂O₃ | Hydrocarbon conversion rate (%) |  |  | 74.4 |  |  |  |  |  |
|  |  | CO₂ removal assumed hydrocarbon conversion rate (%) |  |  | 100.0 |  |  |  |  |  |
| Example B11 | Ru/Mo/Al₂O₃ | Hydrocarbon conversion rate (%) |  | 87.1 |  |  |  |  |  |  |
|  |  | CO₂ removal assumed hydrocarbon conversion rate (%) |  | 100.0 |  |  |  |  |  |  |
| Example B12 | Ru/V/ZrO₂ | Hydrocarbon conversion rate (%) |  |  |  |  |  |  | 87.8 |  |
|  |  | CO₂ removal assumed hydrocarbon conversion rate (%) |  |  |  |  |  |  | 100.0 |  |
| Example B13 | Ru/V/Al₂O₃ | Hydrocarbon conversion rate (%) |  |  |  |  | 78.8 |  |  |  |
|  |  | CO₂ removal assumed hydrocarbon conversion rate (%) |  |  |  |  | 99.9 |  |  |  |
| Example B14 | Ru/V/TiO₂ | Hydrocarbon conversion rate (%) |  |  |  |  |  |  |  |  |
|  |  | CO₂ removal assumed hydrocarbon conversion rate (%) |  |  |  |  |  |  |  |  |
| Example B15 | Ru/Mo/TiO₂ | Hydrocarbon conversion rate (%) |  |  |  |  |  |  |  |  |
|  |  | CO₂ removal assumed hydrocarbon conversion rate (%) |  |  |  |  |  |  |  |  |
| Example B16 | Ni/Al₂O₃ | Hydrocarbon conversion rate (%) |  |  |  |  |  |  |  |  |
|  |  | CO₂ removal assumed hydrocarbon |  |  |  |  |  |  |  |  |

TABLE 10-continued

| | | | conversion rate (%) | | | | | | | |
|---|---|---|---|---|---|---|---|---|---|---|
| | | | Reaction temperature (° C.) | | | | | | | |
| | Catalyst | Indicator | 287 | 289 | 299 | 302 | 308 | 309 | 317 | 331 |
| Example B4 | Ru/Al₂O₃ | Hydrocarbon conversion rate (%) | | | 78.6 | | | 80.8 | | 82.0 |
| | | $CO_2$ removal assumed hydrocarbon conversion rate (%) | | | 99.9 | | | 99.9 | | 99.9 |
| Example B5 | Ru/SiO₂ | Hydrocarbon conversion rate (%) | | | | 3.7 | | | | |
| | | $CO_2$ removal assumed hydrocarbon conversion rate (%) | | | | 46.9 | | | | |
| Example B6 | Ru/MgO | Hydrocarbon conversion rate (%) | | | | | | | | |
| | | $CO_2$ removal assumed hydrocarbon conversion rate (%) | | | | | | | | |
| Example B7 | Ru/TiO₂ | Hydrocarbon conversion rate (%) | | | | | | | | |
| | | $CO_2$ removal assumed hydrocarbon conversion rate (%) | | | | | | | | |
| Example B8 | Ru/Al₂O₃ | Hydrocarbon conversion rate (%) | 88.4 | | | | | | | |
| | | $CO_2$ removal assumed hydrocarbon conversion rate (%) | 100.0 | | | | | | | |
| Example B9 | Ru/Mo/Al₂O₃ | Hydrocarbon conversion rate (%) | | | | | | | | |
| | | $CO_2$ removal assumed hydrocarbon conversion rate (%) | | | | | | | | |
| Example B10 | Ru/V/Al₂O₃ | Hydrocarbon conversion rate (%) | | | | | | | | |
| | | $CO_2$ removal assumed hydrocarbon conversion rate (%) | | | | | | | | |
| Example B11 | Ru/Mo/Al₂O₃ | Hydrocarbon conversion rate (%) | | | | | | | | |
| | | $CO_2$ removal assumed hydrocarbon conversion rate (%) | | | | | | | | |
| Example B12 | Ru/V/ZrO₂ | Hydrocarbon conversion rate (%) | | | | | | | | |
| | | $CO_2$ removal assumed hydrocarbon conversion rate (%) | | | | | | | | |
| Example B13 | Ru/V/Al₂O₃ | Hydrocarbon conversion rate (%) | | | | | | | | |
| | | $CO_2$ removal assumed hydrocarbon conversion rate (%) | | | | | | | | |
| Example B14 | Ru/V/TiO₂ | Hydrocarbon conversion rate (%) | | | | | 81.7 | | | |
| | | $CO_2$ removal assumed hydrocarbon conversion rate (%) | | | | | 99.9 | | | |
| Example B15 | Ru/Mo/TiO₂ | Hydrocarbon conversion rate (%) | | 75.2 | | | | | | |
| | | $CO_2$ removal assumed hydrocarbon conversion rate (%) | | 99.8 | | | | | | |
| Example B16 | Ni/Al₂O₃ | Hydrocarbon conversion rate (%) | | | | | | | 26.7 | |
| | | $CO_2$ removal assumed hydrocarbon conversion rate (%) | | | | | | | 96.2 | |

(Evaluation Test 3)

In the evaluation test 3, a mixed gas ($H_2$/CO=3) containing $H_2$ and CO in a ratio of 3:1 (volume ratio) was used as the reaction gas, the GHSV was set to 2000/h, and the activity test of the hydrocarbon synthesis catalyst cat2 was carried out at the reaction temperature of 235° C. to about 330° C. In this activity test, a catalyst (Examples B17 and B18) in which iron or cobalt was supported on a titania carrier in addition to ruthenium was used. In this case, the reaction gas is an example obtained by assuming a model in which a mixed gas obtained by adding carbon monoxide to hydrogen obtained by electrolyzing water in the electrolytic reaction unit 10, and a mixed gas of hydrogen and carbon monoxide obtained by separating water and carbon dioxide as needed from the gas obtained by carrying out a co-electrolysis reaction of water and carbon dioxide are introduced into the hydrocarbon synthesis reaction unit 30 to carry out the hydrocarbon synthesis reaction.

The results of the evaluation test 3 are illustrated in Table 11.

TABLE 11

| | | | Reaction temperature (° C.) | | | |
|---|---|---|---|---|---|---|
| | Catalyst | Indicator | 235 | 250 | 278 | 327 |
| Example B17 | 2 wt. % Ru/2 wt. % Fe/TiO₂ | $CO_2$ removal assumed hydrocarbon conversion rate (%) | 11.6 | | 99.9 | 99.9 |
| | | $C_1$-$C_4$ calorific value (MJ/Nm³) | 59.0 | | 47.1 | 42.16 |
| Example B18 | 2 wt. % Ru/2 wt. % Co/TiO₂ | $CO_2$ removal assumed hydrocarbon conversion rate (%) | | 99.0 | | |
| | | $C_1$-$C_4$ calorific value (MJ/Nm³) | | 46 | | |

As illustrated in Table 11, it was confirmed that hydrocarbons can be synthesized from a mixed gas containing $H_2$ and CO using a catalyst in which ruthenium and iron or cobalt are supported on a titania carrier as a hydrocarbon synthesis catalyst cat2.

It was confirmed that the above-mentioned hydrocarbon production system 100 can generate a high-calorie gas having a C1-C4 calorific value of 39 MJ/Nm³ or more.

From the above results, as illustrated above, a catalyst in which at least ruthenium is supported as the catalytically active component ca2 on the metal oxide carrier cb2 can be used in the second catalytic reaction unit 30 (hydrocarbon synthesis reaction unit). Further, it is preferable to support at least one of molybdenum, vanadium, iron, and cobalt as the catalytically active component ca2.

It was found that, preferably, the hydrocarbon synthesis catalyst cat2 was a catalyst in which at least ruthenium was supported on the metal oxide carrier cb2, the supported amount of ruthenium was 0.1% by weight or more and 5% by weight or less, and at least one of molybdenum, vanadium, iron, and cobalt as the catalytically active component ca2 was supported on the metal oxide carrier cb2 in addition to ruthenium.

Here, the supported amount of at least one of the molybdenum, vanadium, iron, and cobalt can be 0.2% by weight or more and 6% by weight or less.

Further, in hydrocarbon synthesis catalysts cat2, the adsorption amount of carbon monoxide of the highly active catalyst was 0.4 $\mu ml/g$ or more.

[Heavy Hydrocarbon Separation Unit]

When the gas reaching the heavy hydrocarbon separation unit 35 is cooled, the heavy hydrocarbons contained in the gas released from the hydrocarbon synthesis reaction unit 30 are condensed and the heavy hydrocarbons can be taken out to the outside. For example, in the hydrocarbon synthesis reaction unit 30 using the 2 wt. % Ru/2 wt. % $Fe/TiO_2$ catalyst described in Example B17, when a mixed gas ($H_2/CO=3$) containing $H_2$ and CO in a ratio of 3:1 (volume ratio) was introduced and the reaction was carried out at 275° C., a linear higher aliphatic hydrocarbon having an average chain length of 26 carbon atoms could be extracted from the heavy hydrocarbon separation unit 35. Moreover, when the reaction was carried out at 325° C., a linear higher aliphatic hydrocarbon having an average chain length of 18 carbon atoms could be extracted from the heavy hydrocarbon separation unit 35.

[Water Separation Unit]

A condenser is arranged in the water separation unit 40, and the gas containing $H_2O$ flowing in is adjusted to a predetermined temperature and pressure to be condensed and water is taken out to the outside.

[Carbon Dioxide Separation Unit]

For example, PSA is arranged in this unit 50, and the gas containing $CO_2$ flowing in is adsorbed to the adsorbent under a predetermined temperature and pressure to separate $CO_2$, the separated $CO_2$ is separated from the adsorbent, and thus, $CO_2$ is favorably separated. The separated $CO_2$ can be returned to the front of the electrolytic reaction unit 10 and reused via the carbon dioxide return path 51.

It is also possible to use PSA or the like to make the carbon dioxide separation unit and the water separation unit the same separation unit.

Figure 7:
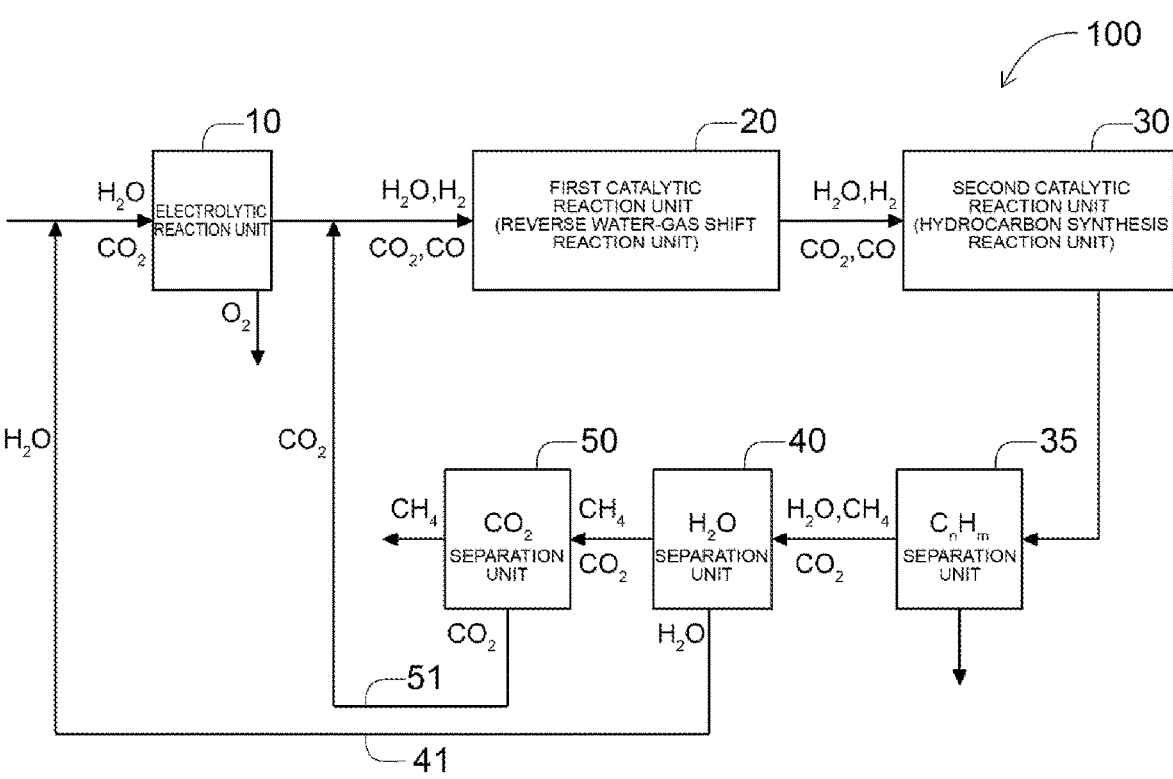
FIG. 7 is a diagram illustrating another configuration of a hydrocarbon production system that guides $CO_2$ to the reverse water-gas shift reaction unit.

Another Embodiment (1) In the above embodiment, $CO_2$ separated in the carbon dioxide separation unit 50 is returned to the front of the electrolytic reaction unit 10. However, in the hydrocarbon production system 100 according to the present invention, since the conversion of $CO_2$ to CO is mainly performed by the reverse water-gas shift reaction unit 20, a return destination of $CO_2$ may be in front of the reverse water-gas shift reaction unit 20. This configuration is illustrated in FIG. 7.

Figure 8:
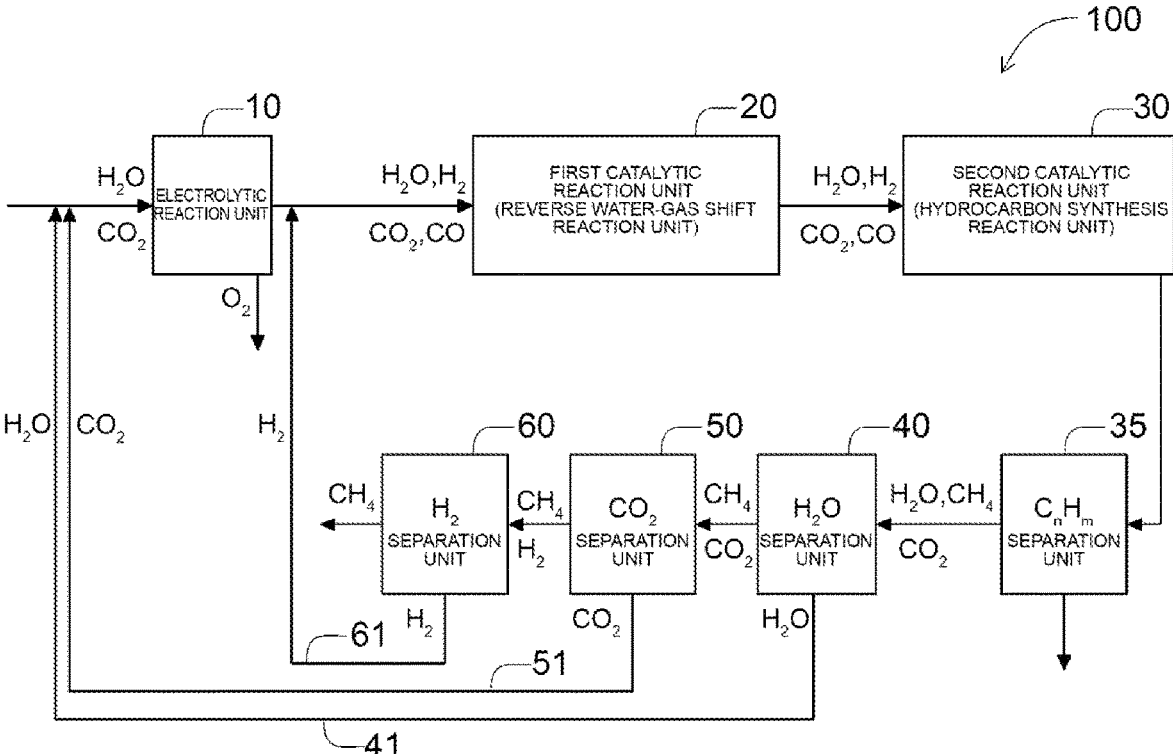
FIG. 8 is a diagram illustrating another configuration of the hydrocarbon production system equipped with the hydrogen separation unit.

(2) In the above embodiment, $H_2$ in the gas obtained from the hydrocarbon synthesis reaction unit 30 is not particularly described. However, a hydrogen separation unit (described as $H_2$ separation unit in the drawing) 60 that separates $H_2$ using a hydrogen separation membrane or the like may be provided to separate $H_2$ and use $H_2$ separately. This configuration is illustrated in FIG. 8. In this example, the return destination of $H_2$ separated by the hydrogen separation unit 60 may be provided in front of the reverse water-gas shift reaction unit 20 so that $H_2$ is used for the reverse water-gas shift reaction.

Figure 9:
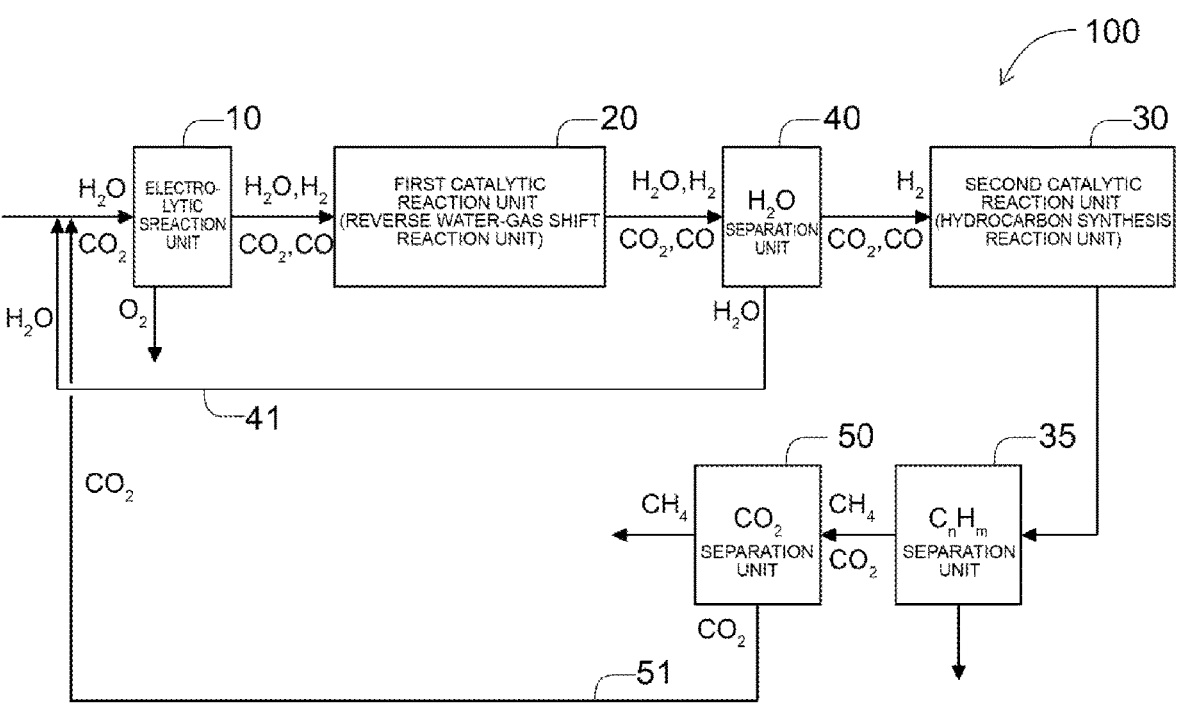
FIG. 9 is a diagram illustrating still another configuration of a hydrocarbon production system equipped with the water separation unit in front of a hydrocarbon synthesis reaction unit.

(3) In the above embodiment, the water separation unit 40 is provided on the lower side of the hydrocarbon synthesis reaction unit 30. However, as illustrated in FIG. 9, the water separation unit 40 may be provided between the reverse water-gas shift reaction unit 20 and the hydrocarbon synthesis reaction unit 30. The main function of the water separation unit 40 is to facilitate the hydrocarbon synthesis reaction.

Figure 10:
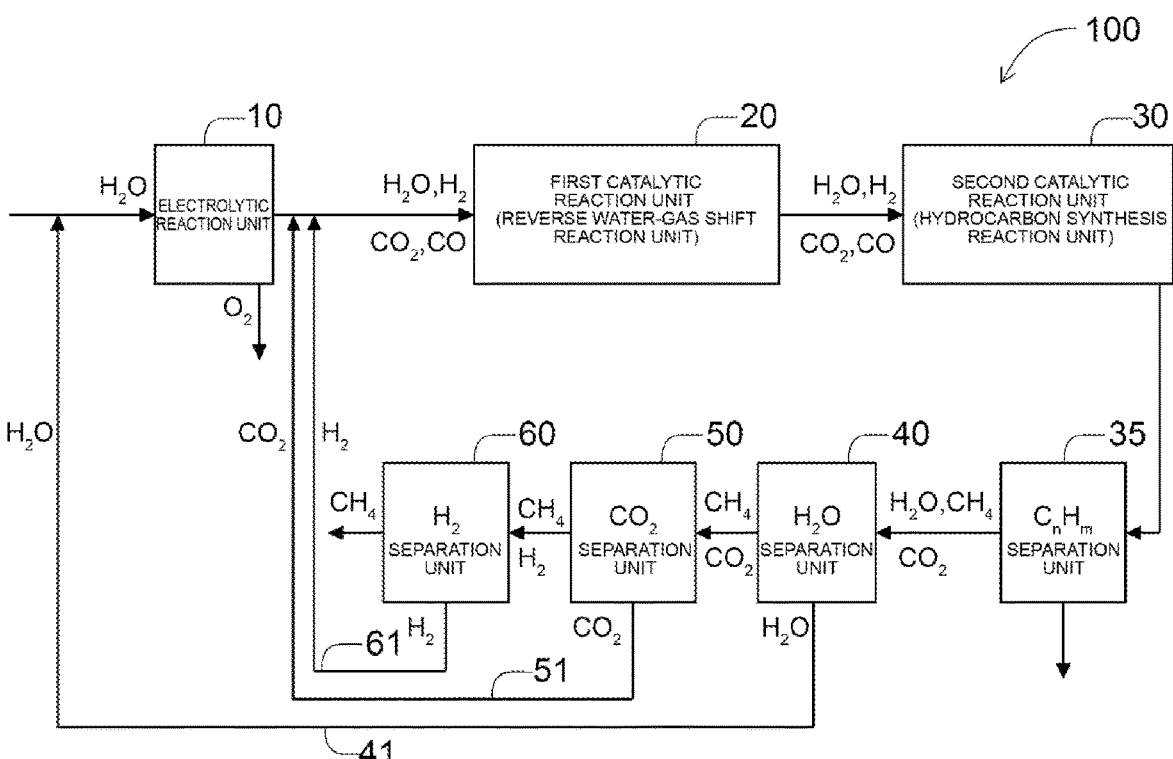
FIG. 10 is a diagram illustrating still another configuration of a hydrocarbon production system in which only water is introduced into the electrolytic reaction unit.

(4) In the above embodiment, an example in which both $H_2O$ and $CO_2$ are supplied to the electrolytic reaction unit 10 and subjected to the electrolysis reaction is illustrated. However, as illustrated in FIG. 10, a system may be used in which only $H_2O$ is supplied to the electrolytic reaction unit 10 to be subjected to the electrolysis reaction. In this case, the carbon consumed in the hydrocarbon synthesis is input to the reverse water-gas shift reaction unit 20 as carbon dioxide.

(5) In the above embodiment, an example in which a solid oxide type electrolytic cell is used as the electrolytic cell 1 in the electrolytic reaction unit 10 is illustrated. However, as the electrolytic cell 1, an alkaline type electrolytic cell, a polymer film type electrolytic cell, or the like may be used.

(6) In the above embodiment, the electrolytic reaction unit 10 and the first catalytic reaction unit 20 are integrated. However, in addition to the reaction units 10.20, the second catalytic reaction unit 30 may be integrated. A configuration example in this case is illustrated in FIG. 13. Incidentally, in FIG. 13, a reference numeral 30a indicates a coating layer of the hydrocarbon synthesis catalyst cat2.

Also, in the case of this configuration, each of the reaction units 10, 20, and 30 can be configured on the metal support 4, and the metal support 4 is supposed to act as a separator for separating the generated hydrocarbon and oxygen.

(7) In the above embodiment, an example of synthesizing a hydrocarbon such as methane in the hydrocarbon synthesis reaction unit 30 is illustrated. However, depending on how the hydrocarbon synthesis catalyst used in the hydrocarbon synthesis reaction unit 30 is selected, it is also possible to synthesize a chemical raw material from hydrogen and carbon monoxide introduced into the hydrocarbon synthesis reaction unit 30.

REFERENCE SIGNS LIST

1: Electrolytic cell
1a: Electrolyte layer
2: Electrode layer
3: Counter electrode layer
4: Metal support (support/separator)
4a: Hole
5: Supply path forming member (separator)
6: Supply path forming member (separator)
10: Electrolytic reaction unit
20: First catalytic reaction unit (reverse water-gas shift reaction unit)
20a: Coating layer

30: Second catalytic reaction unit (hydrocarbon synthesis reaction unit)
40: Water separation unit
50: Carbon dioxide separation unit
60: Hydrogen separation unit
U: Electrolytic cell unit
cat1: Reverse water-gas shift catalyst
ca1: Catalytically active component (active metal)
cb1: Carrier (metal oxide carrier)
cat2: Hydrocarbon synthesis catalyst
ca2: Catalytically active component (active metal
cb2: Carrier (metal oxide carrier)

The invention claimed is:

1. A hydrocarbon production system comprising:
an electrolytic reaction unit into which at least water and carbon dioxide are introduced, the electrolytic reaction unit comprising an electrolysis cell formed on a support, in which an electrode layer and a counter electrode layer are formed with an electrolyte layer interposed therebetween;
an electrode layer-side gas supply path configured to supply water and carbon dioxide to the electrode layer and act as a discharge path configured to discharge hydrogen generated in the electrode layer;
a reverse water-gas shift reaction unit configured to receive a gas containing hydrogen and carbon dioxide that is discharged from the discharge path; and
a hydrocarbon synthesis reaction unit configured to synthesize hydrocarbons from an outlet gas of the reverse water-gas shift reaction unit,
wherein a ratio of hydrogen and carbon monoxide introduced into the hydrocarbon synthesis reaction unit is adjusted by adjusting at least one of the following: a ratio of water and carbon dioxide introduced into the electrolytic reaction unit, reaction conditions of the electrolytic reaction unit, reaction conditions of the reverse water-gas shift reaction unit, or any combination thereof.

2. The hydrocarbon production system according to claim 1, wherein an electrolytic reaction of water is carried out in the electrolytic reaction unit.

3. The hydrocarbon production system according to claim 1, wherein a co-electrolysis reaction between water and carbon dioxide is carried out in the electrolytic reaction unit.

4. The hydrocarbon production system according to claim 1, wherein the reverse water-gas shift reaction unit has a reverse water-gas shift catalyst in which an active metal is supported on a metal oxide carrier.

5. The hydrocarbon production system according to claim 4, wherein the reverse water-gas shift catalyst is a reverse water-gas shift catalyst in which at least one or both of nickel and iron are supported as the active metal on a carrier containing a ceria-based metal oxide or a zirconia-based metal oxide as a main component.

6. The hydrocarbon production system according to claim 5, wherein the ceria-based metal oxide is ceria doped with at least one of gadolinium, samarium, and yttrium.

7. The hydrocarbon production system according to claim 5, wherein the zirconia-based metal oxide is zirconia stabilized by at least one of yttria and scandia.

8. The hydrocarbon production system according to claim 4, wherein copper is supported as the active metal.

9. The hydrocarbon production system according to claim 1, wherein the hydrocarbon synthesis reaction unit has a hydrocarbon synthesis catalyst in which an active metal is supported on a metal oxide carrier.

10. The hydrocarbon production system according to claim 9, wherein the active metal is ruthenium.

11. The hydrocarbon production system according to claim 1, further comprising:
a counter electrode layer-side gas supply path configured to supply a transport gas to the counter electrode layer, wherein the support acts as a separator configured to partition the electrode layer-side gas supply path and the counter electrode layer-side gas supply path.

12. The hydrocarbon production system according to claim 11, wherein the support is a metal.

13. The hydrocarbon production system according to claim 12, wherein the hydrocarbon synthesis reaction unit is supported by the support.

14. A production method of the hydrocarbon production system according to claim 1, the production method comprising disposing an impregnated supported product, which is obtained through an impregnation-supporting step of impregnating a metal oxide carrier with an active metal to be supported on a metal oxide carrier, in the reverse water-gas shift reaction unit and the hydrocarbon synthesis reaction unit.

15. A production method of the hydrocarbon production system according to claim 1, the production method comprising disposing an impregnated supported product, which is obtained through an impregnation-supporting step of impregnating a metal oxide carrier with an active metal to be supported on a metal oxide carrier, in at least a portion of a support to form the reverse water-gas shift reaction unit.

16. A production method of the hydrocarbon production system according to claim 1, the production method comprising at least a calcination step of performing calcination at a temperature of 450° C. or higher in a step of forming the reverse water-gas shift reaction unit.

17. An operation method of the hydrocarbon production system according to claim 1, the operation method comprising performing an operation after subjecting the reverse water-gas shift reaction unit to a reduction pretreatment.

* * * * *